(12) United States Patent  
Visconti

(10) Patent No.: US 10,070,787 B2  
(45) Date of Patent: Sep. 11, 2018

(54) SYSTEM AND METHOD FOR DETECTION AND MONITORING OF A PHYSICAL CONDITION OF A USER

(71) Applicant: Antonio Visconti, Menlo Park, CA (US)

(72) Inventor: Antonio Visconti, Menlo Park, CA (US)

( * ) Notice: Subject to any disclaimer, the term of this patent is extended or adjusted under 35 U.S.C. 154(b) by 0 days.

(21) Appl. No.: 15/893,793

(22) Filed: Feb. 12, 2018

(65) Prior Publication Data

US 2018/0184899 A1 Jul. 5, 2018

Related U.S. Application Data

(63) Continuation-in-part of application No. 15/079,378, filed on Mar. 24, 2016, now Pat. No. 9,888,845.

(60) Provisional application No. 62/187,042, filed on Jun. 30, 2015.

(51) Int. Cl.
| | |
|---|---|
| *A61B 3/14* | (2006.01) |
| *G06K 9/00* | (2006.01) |
| *A61B 3/11* | (2006.01) |
| *A61B 5/00* | (2006.01) |
| *A61B 5/16* | (2006.01) |

(52) U.S. Cl.
CPC ............. *A61B 3/145* (2013.01); *A61B 3/112* (2013.01); *G06K 9/0061* (2013.01); *A61B 5/16* (2013.01); *A61B 5/4845* (2013.01); *A61B 5/7246* (2013.01)

(58) Field of Classification Search
CPC ....... A61B 3/14; A61B 5/0077; A61B 5/1104; A61B 3/1241; A61B 5/026; A61B 5/14555; A61B 5/6821
USPC ............... 351/218, 221, 223, 246, 206, 205
See application file for complete search history.

(56) References Cited

U.S. PATENT DOCUMENTS

2009/0115966 A1* 5/2009 Waldorf ................. A61B 3/112  
351/210

* cited by examiner

*Primary Examiner* — Hung Dang  
(74) *Attorney, Agent, or Firm* — William E. Nuttle

(57) ABSTRACT

A system and method are provided for detecting and monitoring Pupillary Light Reflex responses and physical conditions using a portable video capture device (PVCD) for the purpose of diagnosing or monitoring impairment due to consumption of intoxicating substance or neurological disorder due to trauma or illness. In one embodiment, the PVCD is placed in an opaque enclosure, and positioned over one or both eyes. Video of the eyes is captured over a predetermined time using a video camera of the PVCD, and the video processed to measure changes in a feature of at least one eye. Data from the measured changes is analyzed together with additional physical data collected on a condition of the user, to estimate a degree of impairment. The degree of impairment and additional physical data is output to the user through a user interface in the PVCD and stored in local and remote memory for monitoring.

20 Claims, 19 Drawing Sheets

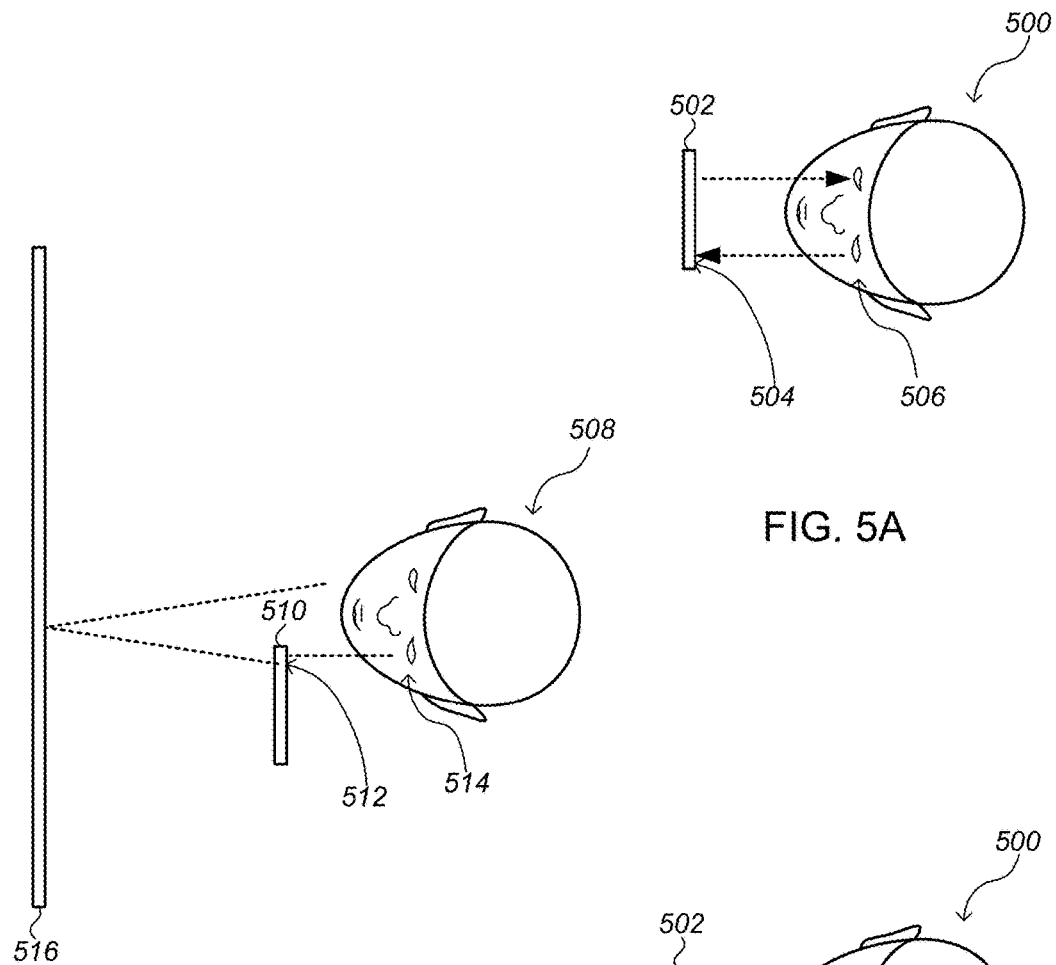
FIG. 5A
FIG. 5B
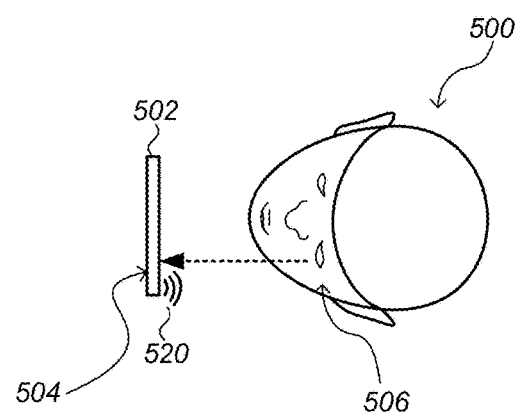
FIG. 5C

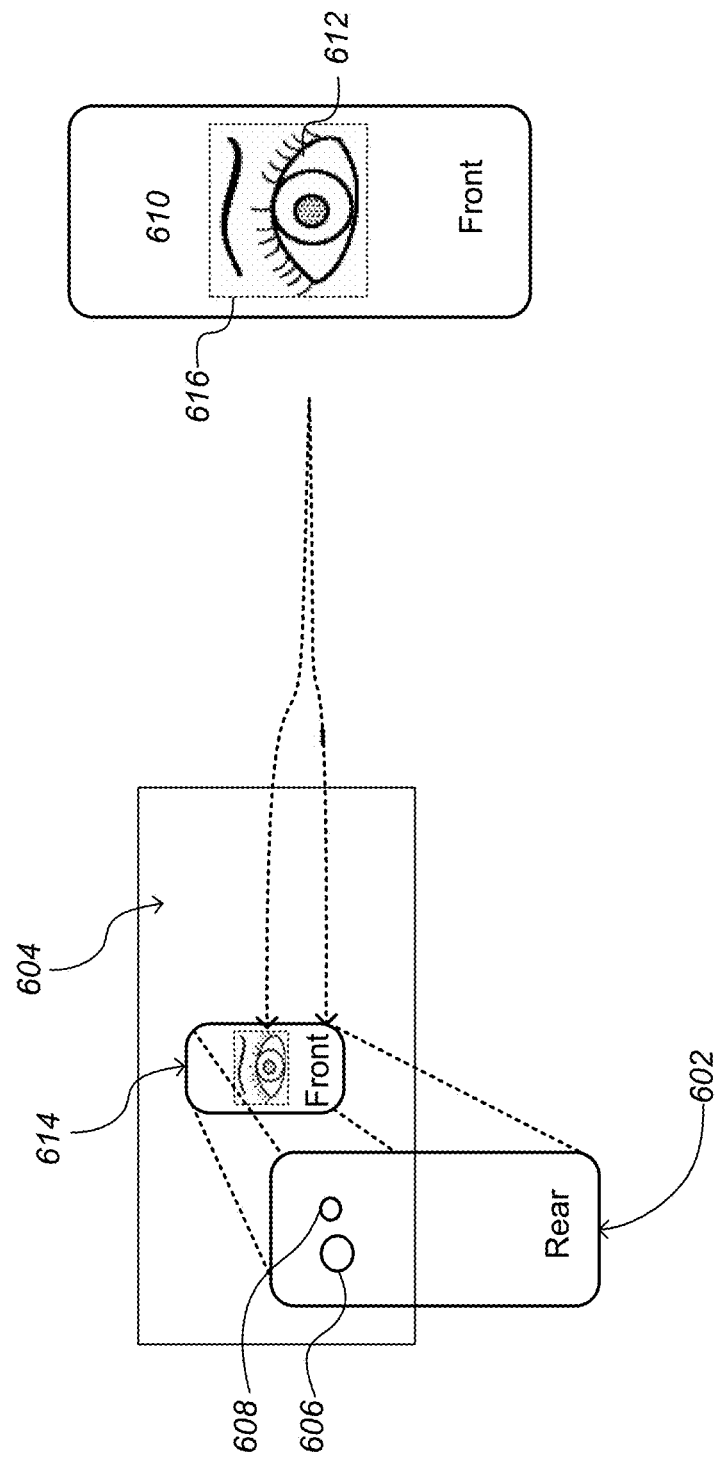

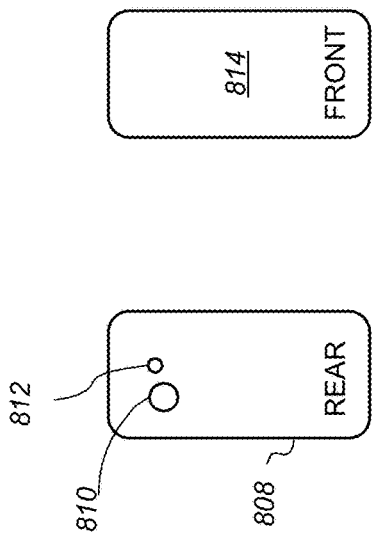
FIG. 8A
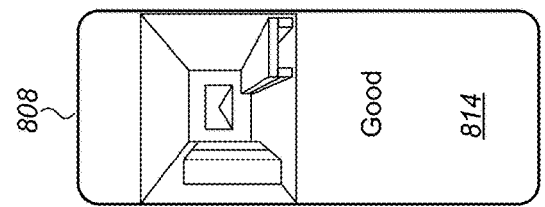
FIG. 8B
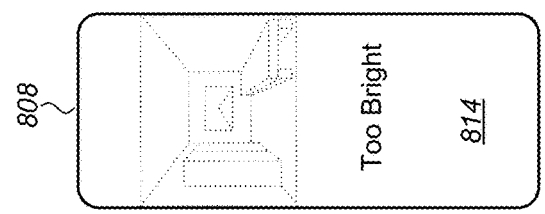
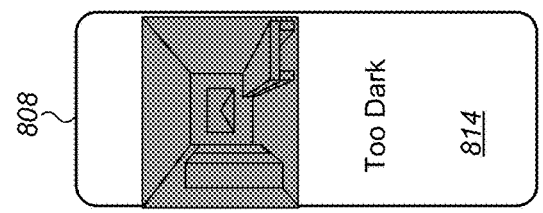
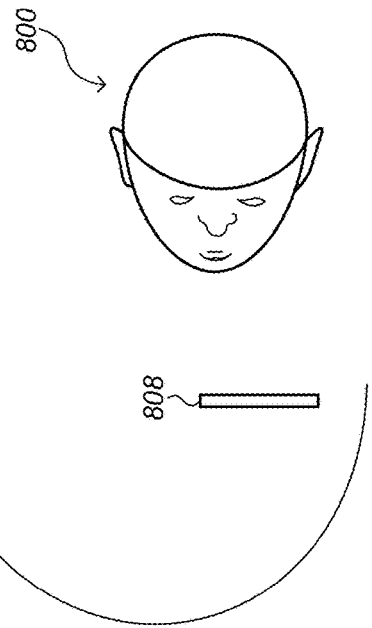
FIG. 8C

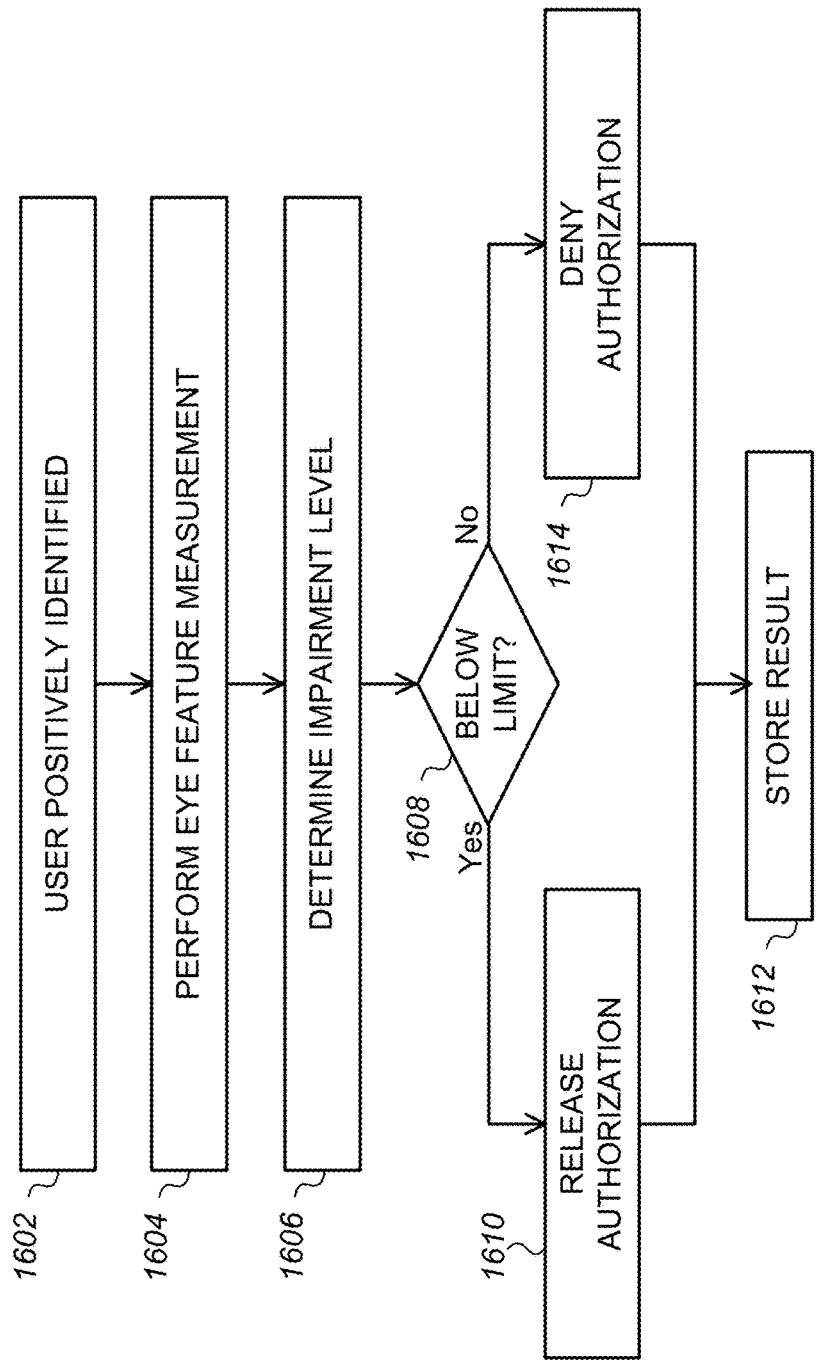

SYSTEM AND METHOD FOR DETECTION AND MONITORING OF A PHYSICAL CONDITION OF A USER

CROSS-REFERENCE TO RELATED APPLICATIONS

This application is a continuation-in-part of U.S. application Ser. No. 15/079,378, filed Mar. 24, 2016, now U.S. Pat. No. 9,888,845, claims the benefit of priority under 35 U.S.C. 119(e) to U.S. Provisional Patent Application Ser. No. 62/187,042, filed Jun. 30, 2015, both of which are incorporated herein in their entirety.

TECHNICAL FIELD

The present disclosure relates generally to a system and method for detection of a physical condition of a user, and more particularly to a method, system and application or software program designed to permit a user to optically detect a physical condition, including impairment and/or neurological disorders that affects an individual Pupillary Light Reflex (PLR), using a portable video capture device, will refer to all such conditions as impairment.

BACKGROUND

The pupillary light reflex (PLR) is a reflex that controls the diameter of the pupil, in response to the intensity of light that falls on the retinal ganglion cells of the retina in the back of the eye, thereby assisting in adaptation to various levels of lightness/darkness. A greater intensity of light causes the pupil to constrict, whereas a lower intensity of light causes the pupil to dilate. Thus, the pupillary light reflex regulates the intensity of light entering the eye. It is well documented in the medical and scientific community that an individual PLR may be altered by ingesting or otherwise introducing an intoxicating substance, such as alcohol or a drug, or by a medical condition such as a concussion or by other neurological disorders such as diabetic neuropathy. Thus, the analysis of the PLR can be used to detect impairment due to intoxicating substances and/or all neurological disorder affecting an individual PLR response.

Impairment can be brought about by or the result of ingesting or otherwise introducing an intoxicating substance, such as alcohol or a drug, a neurological disorder can be caused by a medical condition such as a concussion or by other pathologies like diabetic neuropathies. By impairment it is meant a diminution of a speed or quality in mental and motor functions of the effected individual. Impairment can include or result in loss or diminishment in judgment, self-control, reasoning, memory, speech and/or coordination. By neurological disorder is meant any disorder of the nervous system.

Extreme impairment is readily recognizable to others, and, generally, to the individual—although because judgment is impaired the individual may not recognize or acknowledge the impairment. More problematic are situations in which the individual is only mildly impaired and thus may not be aware of any impairment at all. For example, because of a multitude of factors that affect blood alcohol concentration, i.e., age, gender, rate of consumption, body mass, food consumption and alcohol intolerance common among some ethnic groups, it is very difficult for an individual to assess his or her own impairment. While earlier stages of alcohol impairment may be undetectable to the drinker and others, it is known even small amounts of alcohol may affect one's ability to drive, and a person will possibly be too impaired to drive or perform a dangerous task before appearing or maybe even feeling "drunk" or "high."

The same situation can arise when a person has suffered a blow to the head and have a concussion or is suffering from extreme fatigue, but insist that they 'feel fine,' and do not require medical attention or rest.

Chronic illnesses like diabetes are known to cause diabetic neuropathies that alter the PLR response over time. People with diabetes can, over time, develop nerve damage throughout the body. The change is subtle and slow and some people with nerve damage have no symptoms.

Thus, there is a need for an easy to use, portable and ubiquitous system and method to permit a person to measure the Pupillary Light Reflex response in themselves and others and correlate such measurement to a degree of impairment due to the assumption of impairing substances and/or to a neurological disorder for diagnostic, screening, authorization and/or monitoring purposes.

SUMMARY

The objective of the invention is to provide a non-invasive, portable way to measure Pupillary Light Reflex (PLR) response and other involuntary eye movements and correlate such measurement to an impairment level that can be associated with fatigue, alcohol, drug consumption, trauma and/or other neurological disorder due to any possible cause that affects the individual PLR response. An important aspect of the invention is the implementation of it on a Portable Video Capture Devices like a Smartphone, a Personal Digital Assistant or a Tablet Computer that may be carried by users on a regular basis for communication, entertainment, business or any other purpose.

Having the system implemented in such way significantly increase its use and benefits. Users can self-test and do not have to plan to carry or procure an expensive dedicated instrument like a stand-alone pupilometer to detect, measure and/or monitor over time their PLR response or relay only on individual judgment to make such assessment.

Another important aspect of the invention is the implementation of a Smart User Interface (SUI) that will collect additional information by interacting with the user. The information collected includes physical characteristics like weight, height, sex, ethnicity, and other physical information as well specific information regarding the type of activities performed and the product consumed at the time preceding the test. If needed, the SUI may guide the Users to perform additional tests according to the capabilities of the PVCD to complement the PLR data. Examples of additional measurements that can be performed are hand tremor, pulse and and/or any other physical data measured with the PVCD with or without additional attachments. For example, the PVCD can be paired with a separate wearable device, such as a fitness tracker or watch, capable of measuring one or more of a hand tremor, pulse rate, oxygenation level, and irregular heartbeat. The data is saved in a local database or data-store on the device and/or remotely to a server location and processed to construct a Reference Data Set by a Correlation and Prediction Process that will subsequently use the reference data set to extrapolate, at test time, an impairment level and provide guidance to the user.

Upon establishment that the subject under test may have an impairment level that may require medical attention the SUI will be able to connect to network enabled transportation and/or emergency services, providing location data and other information for pick up and/or assistance of the impaired subject. Additionally, the system may connect with a remote medical professional that will interact with the User under test via audio and/or video connection to make further analysis for diagnostic, screening, authorization and/or monitoring purposes.

Furthermore, the invention may be used in safety sensitive environments, where for safety and liability reasons, an employee starting a working shift is required to self-test and submit the result to an employer to receive authorization to start working. In such environment a positive identification of the subject under test is required and achieved via a bio metric measurement identifying unique characteristics of the eye on the same video captured with PVCD used for establishing impairment.

BRIEF DESCRIPTION OF THE DRAWINGS

Embodiments of the present invention will be understood more fully from the detailed description that follows and from the accompanying drawings and the appended claims provided below, where:

FIGS. 5A through 5C illustrate free-hand methods to perform video capture using different types of PVCDs according to embodiments of the present disclosure;

FIGS. 6A and 6B illustrate in greater detail a method to perform video capture using a PVCD having a rear facing camera and light source according to an embodiment of the present disclosure;

FIGS. 8A through 8C illustrate methods for using a light meter software to improve video capture according to embodiments of the present disclosure;

FIG. 16 is a flowchart illustrating a method to perform user authorization according to an embodiment of the present disclosure;

DETAILED DESCRIPTION

The present disclosure is directed generally to a system and method for testing for individual impairment due to the influence of alcohol, drugs, an injury, fatigue and/or or other neurological disorder due to any possible cause that affects an individual PLR response. The invention may be utilized to detect impairment due to the consumption of impairing substances like alcohol, marijuana or other drugs, early sign of potential neurological damage following a trauma event like a concussion or monitor the progress of a neurological disorder like a diabetic neuropathy In one embodiment, the system and method uses an add-on opaque enclosure to position the PVCD and control light conditions for optimal video capture of at least one eye, to detect involuntary eye movement or reflex that are affected by fatigue, the consumption of alcohol, drugs, trauma, or other neurological disorder due to any possible cause that affects an individual PLR response and to inform users and/or a monitoring service and/or a medical professional of the impairment level for diagnostic, screening or monitoring purposes. Said involuntary eye movements can include pupil size changes due to light stimuli called Pupillary Light Reflex and small, jerk-like, involuntary eye movements called saccadic eye movements.

In the following description, for purposes of explanation, numerous specific details are set forth in order to provide a thorough understanding of the present invention. It will be evident, however, to one skilled in the art that the present invention may be practiced without these specific details. In other instances, well-known structures, and techniques are not shown in detail or are shown in block diagram form in order to avoid unnecessarily obscuring an understanding of this description.

Reference in the description to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment. The term to couple as used herein may include both to directly electrically connect two or more components or elements and to indirectly connect through one or more intervening components.

Figure 1:
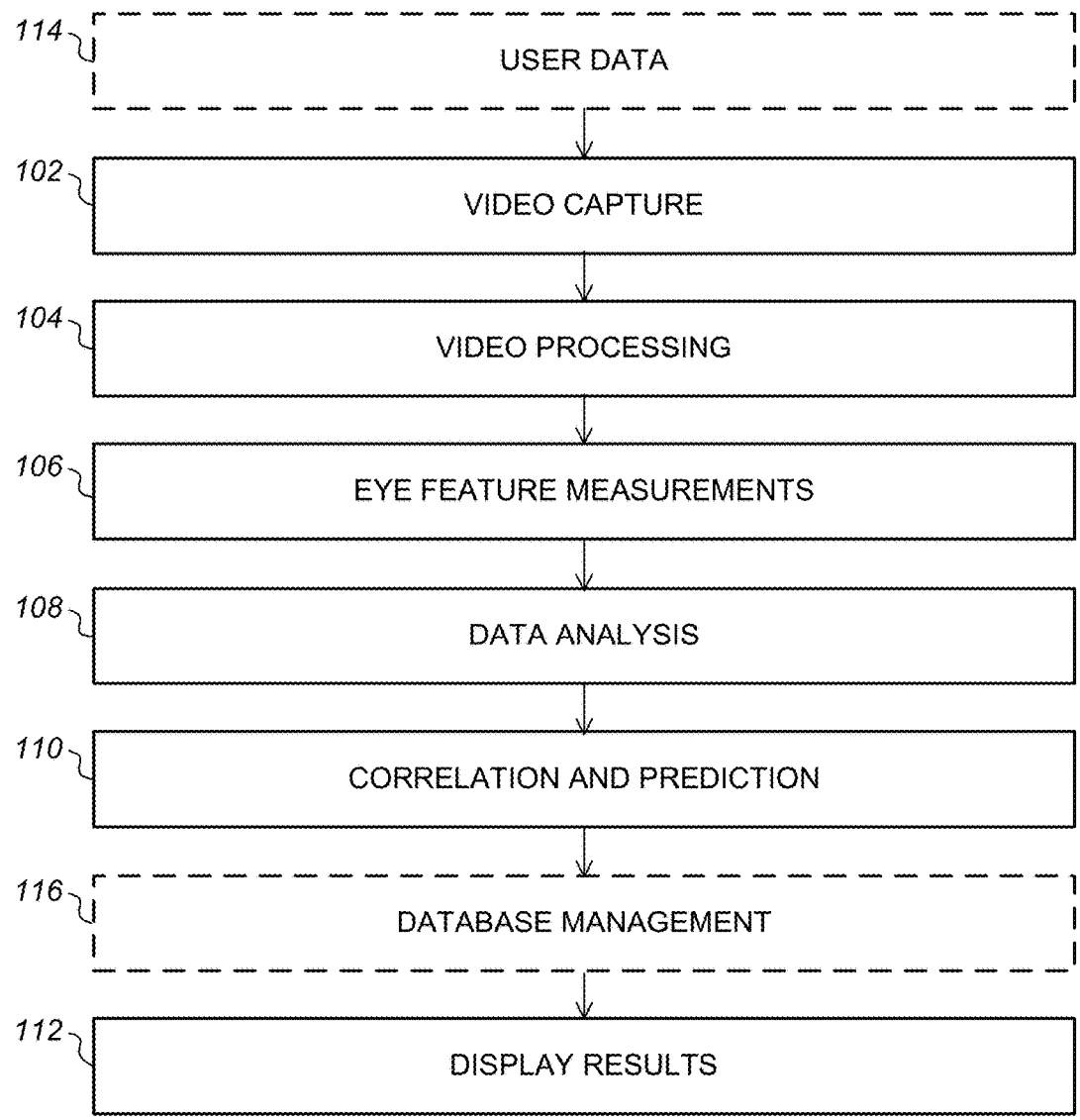
FIG. 1 is a flowchart illustrating a method to perform an impairment test according to an embodiment of the present disclosure.

FIG. 1 is a flowchart illustrating the most general embodiment of a method to perform a PLR response test of a person according to an embodiment of the present disclosure. Each of the steps or block illustrated in FIG. 1 will be described in greater detail below with reference to FIGS. 2 through 13.

Referring to FIG. 1, the method begins with capturing video or multiple images of an eye exposed to light stimuli over a predetermined time using a video camera of a portable video capture device or PVCD (102). Next, the captured video is processed to locate a feature of the eye (104). Features of the eye can include a pupil, an iris and/or a border between the pupil and the iris or any other discernible feature. A change in the located feature in response to the light stimuli over the predetermined time is measured (106). Next, data extracted from the measured change in the feature is analyzed (108). The data analysis can include calculating a number of parameters from the extracted data. Next, the calculated parameters are correlated with predetermined reference parameters in a data-store and a probability and degree of impairment predicted based on the results of the correlation (110). Finally, the resultant probability and degree of impairment of the person, is output through a user interface in the PVCD, such as a display and/or auditory interface to a user (112). It is noted that user may be the person undergoing the impairment test or another individual.

Optionally, as shown in FIG. 1, the method may further include an initial step of receiving from the user data on the person undergoing the impairment test (114), and updating or managing the data-store (116) with the resultant probability and degree of impairment of the person following the correlation and prediction step (110). User data can include a name of the person undergoing the impairment test, contact information, age, gender, height, weight, body mass, ethnicity, and other information required for the correlation and prediction step. The data-store may include a local data-store stored in a local memory of the PVCD, and/or a remote data-store stored in a remote memory coupled through a network to a network enabled PVCD.

Figure 2:
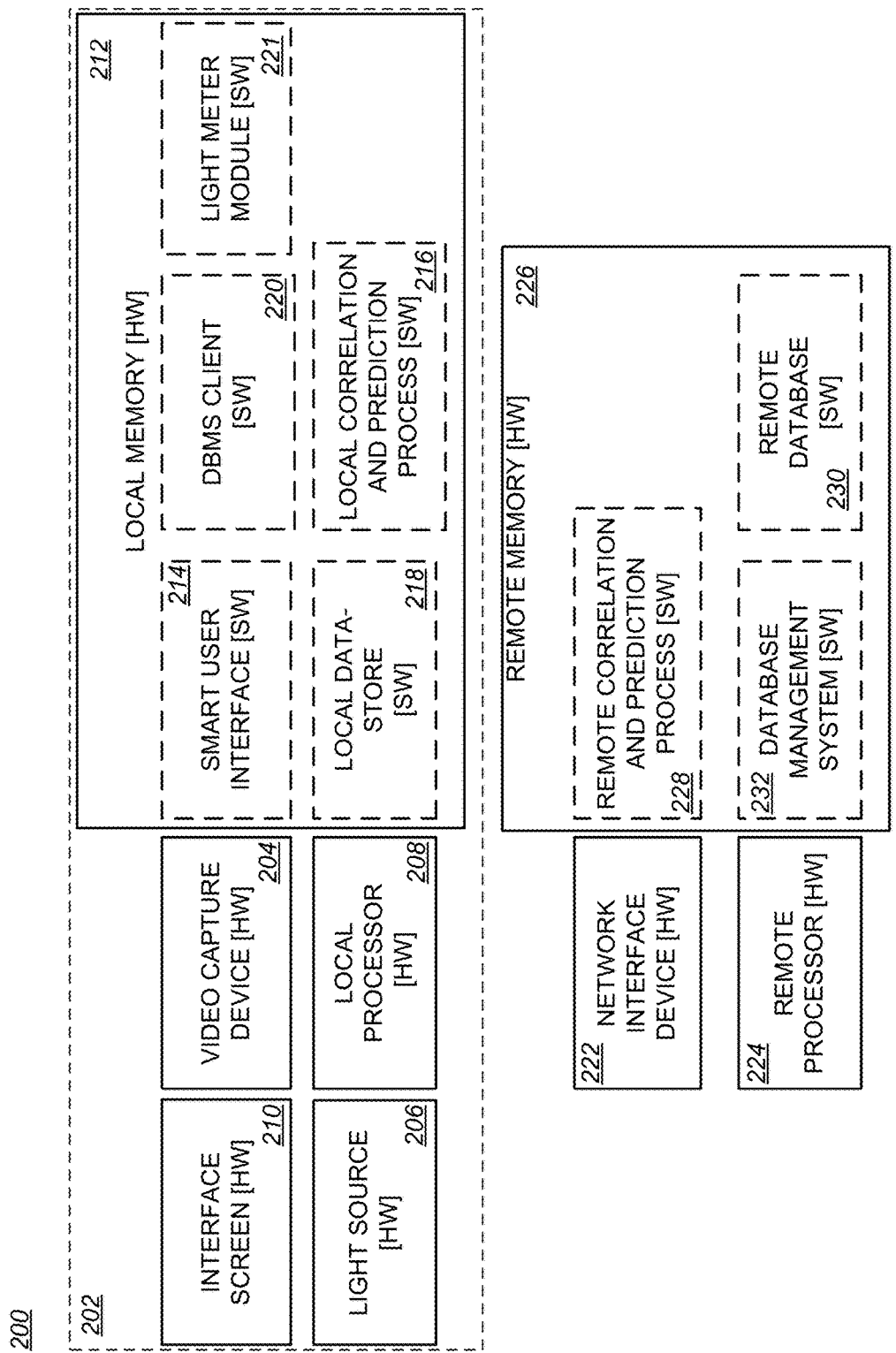
FIG. 2 illustrates a block diagram of a system according to an embodiment of the present disclosure.
Figure 3:
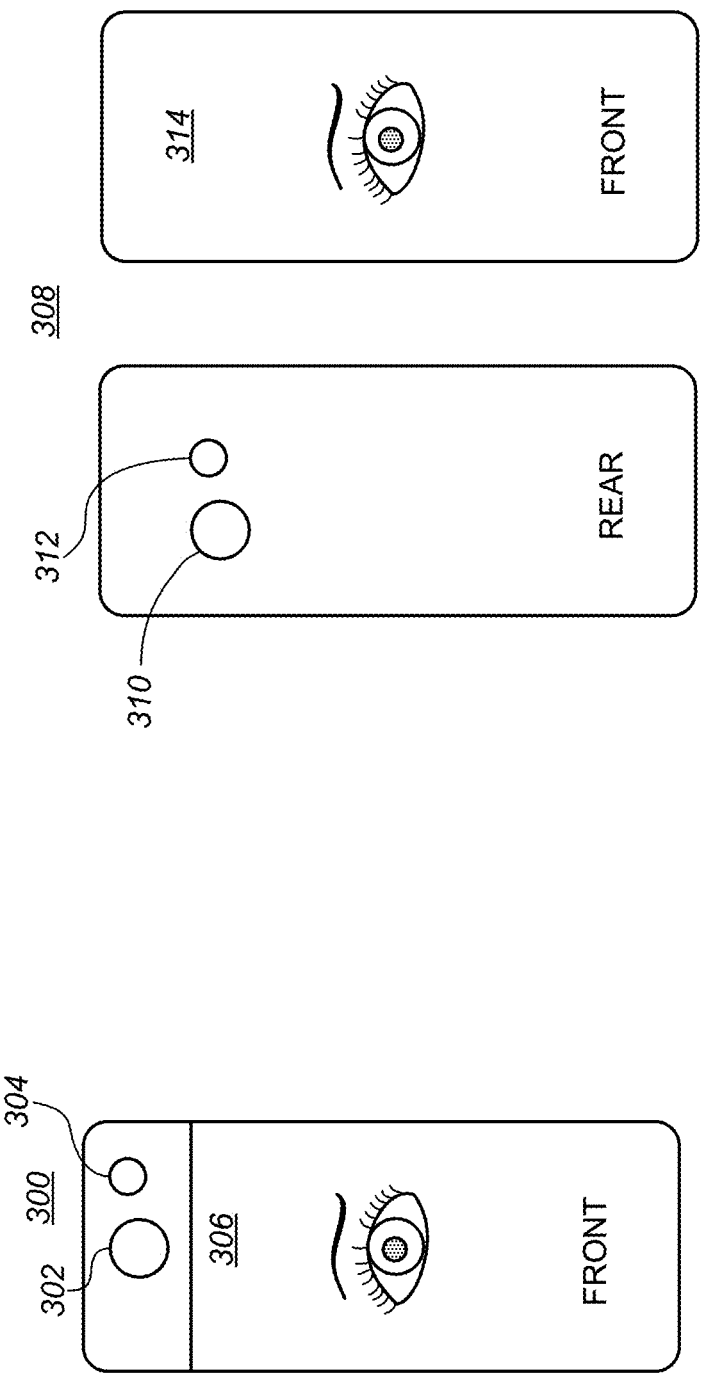
FIGS. 3A and 3B illustrate Portable Video Capturing Devices (PVCDs) suitable for use with the system and method of the present disclosure.

FIG. 2 illustrates a block diagram of a system 200 for performing an impairment test according to an embodiment of the present disclosure. Referring to FIG. 2 the system 200 generally includes a PVCD 202 having a video camera or video capture device 204, a light source 206, a local processor 208, a hardware interface 210, and a local memory 212. The video capture device 204 is configured or adapted to capture video over a predetermined time of an eye exposed to light stimuli generated by the light source 206. The local processor 208 is configured or adapted to execute a software program or application to locate and measure a change in a feature of the eye over the predetermined time, analyzing the changes and extracting data therefrom, calculating a number of parameters from the extracted data, and correlating the calculated parameters with predetermined reference parameters to predict a probability and degree of impairment. The hardware interface 210 can include a display and/or auditory device, to communicate to a user the probability and degree of impairment.

The local memory 212 can store software (SW) including user interface SW 214, local correlation and prediction process SW 216, a local data-store 218, data-store management system (DBMS) client SW 220 and light meter software or module (LMM) 221. The user interface SW or module 214 includes computer program code to communicate with the user via the hardware interface. The local correlation and prediction process SW 216 includes computer program code executed by the processor to locate and measure a change in a feature of the eye, analyze and extract data from the changes, and calculate and correlate a number of parameters with predetermined reference parameters to predict a probability and degree of impairment. The local data-store 218 includes computer program code to store and retrieve information necessary to perform the impairment test, including predetermined reference parameters and, optionally user data on the person undergoing test. The DBMS client SW 220 includes computer program code to update or managing the local data-store 218 with customized parameters used by the correlation and prediction process to calculate the resultant probability and degree of impairment of the person following the correlation and prediction step and store and maintain historical measurement data. The light meter module 221 includes computer program code to direct the user to reduce the impact of environmental or ambient light improving the video capture.

Optionally or preferably in some embodiments, such as that shown, the PVCD is a network enabled PVCD and the system 200 can further includes a network interface device 222, that connects to a cellular telephone tower or a wireless access point, through which the network enabled PVCD can be coupled to a remote processor 224 and/or a remote memory 226. Like the local processor 208, the remote processor 224 can be configured or adapted to execute one or more software programs including programs to locate and measure a change in a feature of the eye over the predetermined time, analyze the changes and extracting data therefrom, calculate a number of parameters from the extracted data, and correlate the calculated parameters with predetermined reference parameters to predict a probability and degree of impairment.

The remote memory 226 can store software (SW) including remote correlation and prediction process SW 228, a remote data-store 230, and data-store management system (DBMS) SW 232. The remote correlation and prediction process SW 228 includes computer program code executed by the processor to locate and measure a change in a feature of the eye, analyze and extract data from the changes, and calculate and correlate a number of parameters with predetermined reference parameters to predict a probability and degree of impairment. The remote data-store 230 includes computer program code to store and retrieve information necessary to perform the impairment test, including predetermined reference parameters and, optionally user data on the person undergoing test. The DBMS SW 230 includes computer program code to update or managing the remote data-store 230 with the resultant probability and degree of impairment of the person following the correlation and prediction step. It will be understood that the remote processor 224 and the remote data-store 232 can be desirably used to maintain and update data of all users of the system for the purpose of analyzing measurements and results over the large user base. The data is used for a continuous refinement of the correlation and prediction process.

Suitable PVCDs for use with the system and method of the present disclosure may include any portable, electronics device with video capture capability, a light source and a user interface, including, for example, a smartphone, a portable computer, personal digital assistant, a digital video camera, or a tablet computer. Preferably, the PVCD further includes a processor and is network enabled.

FIGS. 3A and 3B illustrate two different embodiments of smartphones suitable for use as PVCDs in the system and method of the present disclosure. Referring to FIG. 2A in the first embodiment the PVCD is a smartphone 300 having a front-facing video camera 302 and light source 304. By front-facing it is meant the video camera and light source are on the same side of the smartphone as a view-finder and interface screen or display 306. It will be understood that this arrangement or configuration is particularly advantageous when the user and the person undergoing impairment testing are one and the same, i.e., for self-testing, as it simplifies the video capture process. Although, the system and method of the present disclosure are tolerant of movement during the predetermined time in which video is captured, generally the results are improved if the user can maintain the relative position of the eye to the camera throughout the predetermined time.

However, many current and previous generations of smartphones either do not include a front-facing video camera and light source, or a resolution of the front facing video camera is too low to work with the system and method of the present disclosure. Thus, in another embodiment, shown in FIG. 3B, the PVCD is a smartphone 308 having a rear-facing video camera 310 and light source 312. By rear-facing it is meant the video camera and light source are on the opposite side of the smartphone from the view-finder and interface screen or display 314. It will be understood that this arrangement or configuration is particularly advantageous when the user and the person undergoing impairment testing are not the same, i.e., when a first person, the user, tests another, as it simplifies the video capture process. This embodiment is particularly advantageous when the suspected impairment is the result of fatigue or a medical condition, such as a concussion, which may make it difficult for a self-testing user to maintain the relative position of the eye to the camera throughout the predetermined time. It will further be understood, that this embodiment can still be used for self-testing by use of a mirror or reflecting surface, and/or a removable positioning device (not shown in this figure) used with the smartphone, and/or with an embedded real-time eye position detection processing providing audio feedback to user which will be described in greater detail below.

Suitable for PVCD with access to camera real time parameters like focus distance, lens position and other significant parameters and/or real time video processing capability. The distance of the PVCD from the user under test is estimated by analyzing in real time the retrieved camera parameters and/or video frames and provide visual and/or audible and/or haptic guidance to the user to adjust a distance between the eye and the camera of the PVCD.

Figure 4:
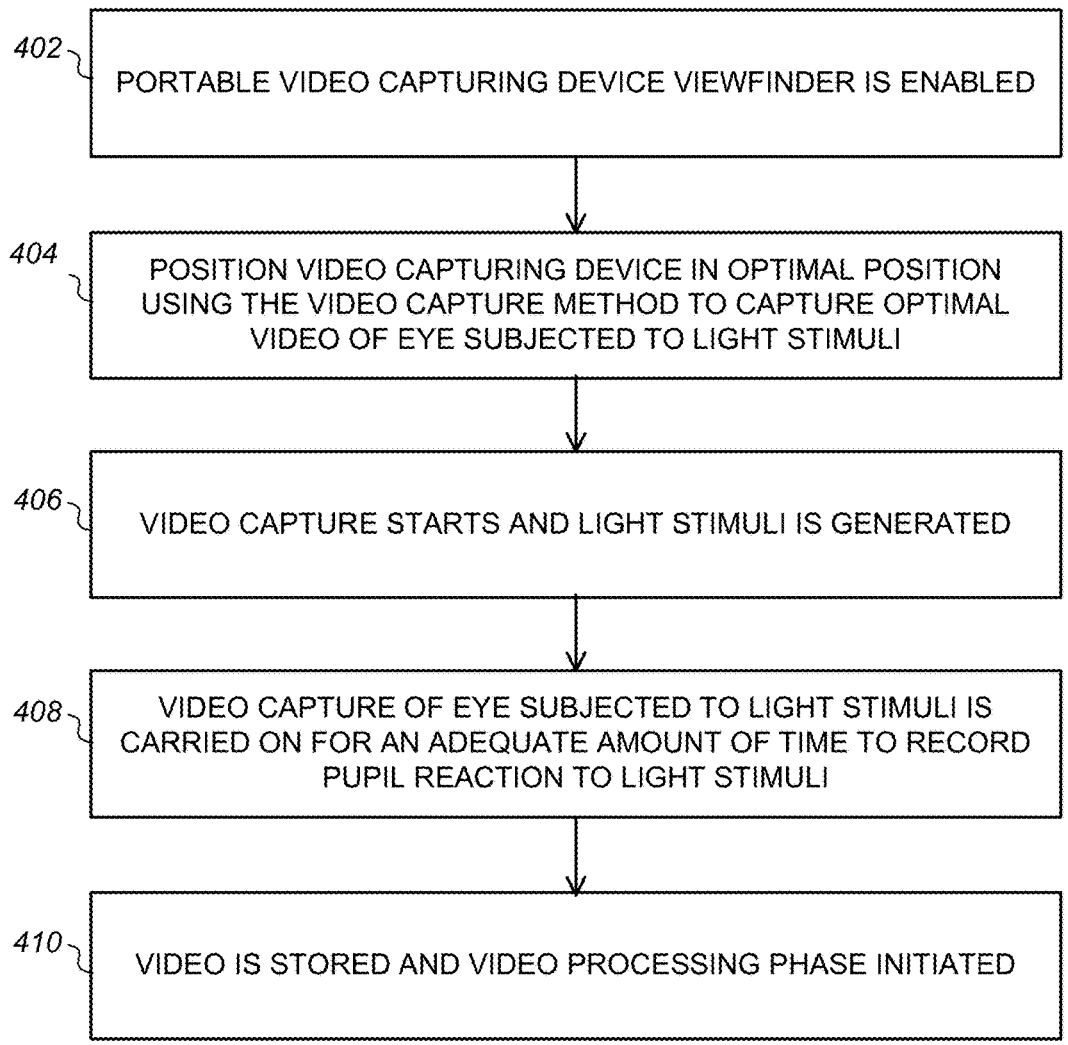
FIG. 4 is a flowchart illustrating a method to perform video capture according to an embodiment of the present disclosure.

Methods of performing video capture according to the system and method of the present disclosure will now be described with reference to FIGS. 4 through 6B. FIG. 4 is a flowchart illustrating a method to perform video capture according to one embodiment of the present disclosure. Referring to FIG. 4, the method begins with a user enabling a viewfinder of the PVCD (402). The user then positions the PVCD in an optimal position (described in greater detail below with reference to FIG. 7) to capture video of an eye of the person undergoing test and subjected to light stimuli (404). Next, video capture starts and a light stimulus is generated (406). Video capture of eye subjected to light stimuli is carried on for a predetermined amount of time to record pupil reaction to light stimuli (408). The video is then stored and video processing phase is initiated (410).

FIGS. 5A, 5B and 5C illustrate free-hand methods to perform video capture using different types of PVCDs according to embodiments of the present disclosure.

FIG. 5A illustrates a free-hand method in which a user 500 and the person undergoing impairment testing are one and the same, i.e., for self-testing, using a PVCD (smartphone 502) having a front-facing video camera and light source on the same side of the smartphone as a view-finder and interface screen or display 504. This configuration enables the user to maintain the relative position of an eye 506 to the camera throughout the predetermined time.

FIG. 5B illustrates another free-hand method in which the user 508 and the person undergoing impairment testing are one and the same, i.e., for self-testing, using a PVCD (smartphone 510) having a rear-facing video camera and light source on the opposite side of the smartphone as a view-finder and interface screen or display 512. This configuration enables the user to maintain the relative position of an eye 514 to the camera throughout the predetermined time using a mirror 516.

FIG. 5C illustrate another free-hand method suitable for PVCD with real time access to camera parameters like focus distance, lens position and other significant parameters and/or real time video processing capability. This embodiment further uses an audible device, such as a speaker in the PVCD to produce an audible signal 520 to provide audible and/or visible guidance based on the reading of the camera parameters and/or data from real time processing of video frames. This configuration enables the user to maintain the relative position of an eye 506 to the camera throughout the predetermined time, without the use of mirror or viewfinder screen. This configuration can be used for PVCD with either rear or front facing camera and light source FIGS. 6A and 6B illustrate in greater detail a method for optimal self-capture video of own eye using a PVCD having a rear facing camera and light source, such as the embodiment of FIG. 5B above. Referring to FIGS. 6A and 6B, the method consists of a dedicated Smart User Interface software (SUI) running on the PVCD 602 and the use of a mirror 604 to guide a user to correctly a PVCD having a rear facing camera 606 and light source 608 to perform an optimal video capture operation. The user will position him or herself in front of the mirror 604 to interact with the viewfinder and input screen 610 while pointing the camera and light source to own eye 612 for video capture. The SUI will guide the user by providing positioning instruction in a mirrored fashion in order to make them appear normal in the mirror reflection 614. The SUI can also display a framing mask 616 to guide the user to position the PVCD at the optimal distance for video capture. The size and position of the eye as seen in the framing mask provides the necessary feedback to user for optimal positioning of PVCD. Optionally, the SUI can also provide instructions in an audible form, utilizing the sound capability of the smartphone PVCB.

Figure 7A:
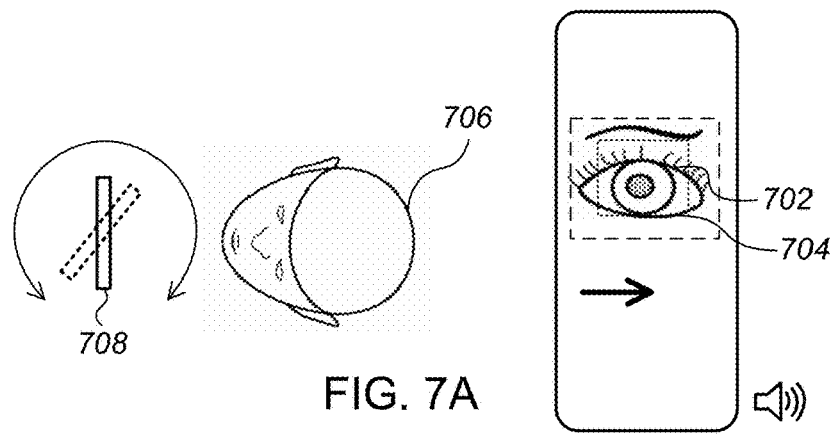
FIGS. 7A through 7C illustrate methods for providing feedback to improve accuracy in free-hand methods to perform video capture according to embodiments of the present disclosure.
Figure 7B:
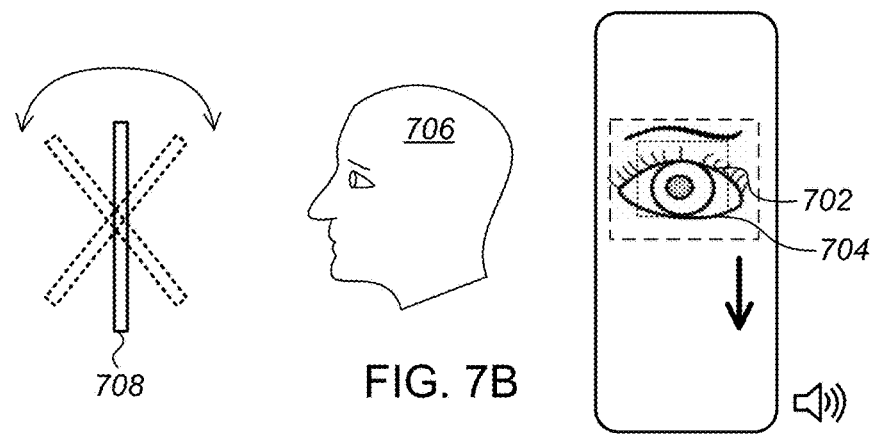
Figure 7C:
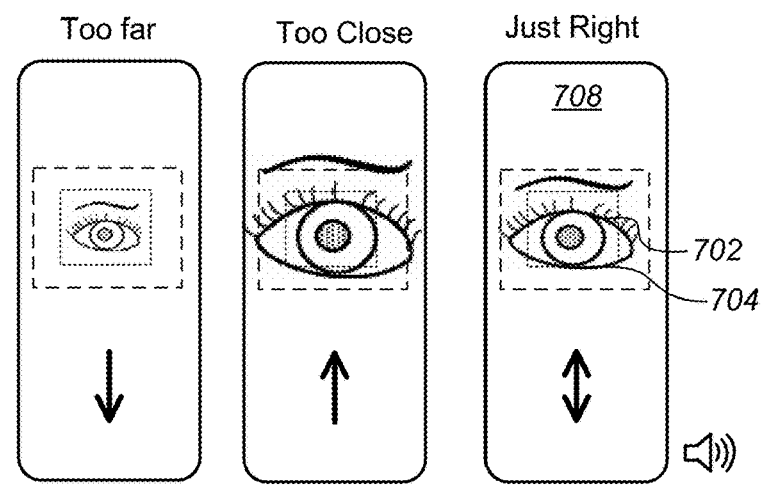

In either embodiment, i.e., a PVCD having rear facing camera or a front facing camera, the accuracy of the measurement is affected by the hand movements of the user holding the PVCD. FIGS. 7A through 7C illustrate in greater detail how the SUI can use PVCD sensors data from accelerometer, gyroscope, magnetometer and/or an image of the eye 702 in relation to framing mask 704 to guide in real time a user 706 to optimal positioning of the PVCD 708. In particular, FIG. 7A illustrates how the SUI can provide rotation feedback in visual and/or audible form. FIG. 7B illustrates how the SUI can provide tilt feedback in visual and/or audible form. And FIG. 7C illustrates how the SUI can provide distance feedback in visual and/or audible form.

FIGS. 8A through 8C illustrate methods for using the light meter module (LMM) to direct the user to reduce the impact of environmental or ambient light improving the video capture. Referring to FIG. 8A in one embodiment, the PVCD is a smartphone 808 having a rear-facing video camera 810 and light source 812. By rear-facing it is meant the video camera and light source are on the opposite side of the smartphone from the view-finder and interface screen or display 814. Referring to the left hand figure of FIG. 8B it is seen that the environmental or ambient light is too dark negatively impacting video capture. Similarly, the middle figure of FIG. 8B illustrates a condition in which the environmental or ambient light is too bright. FIG. 8C illustrates how the use may be prompted using either visual and/or audible signal from the PVCD to reposition him or herself relative to ambient light to provide a condition in which the environmental or ambient light provides a good video capture—illustrated in FIG. 8C.

Figure 9B:
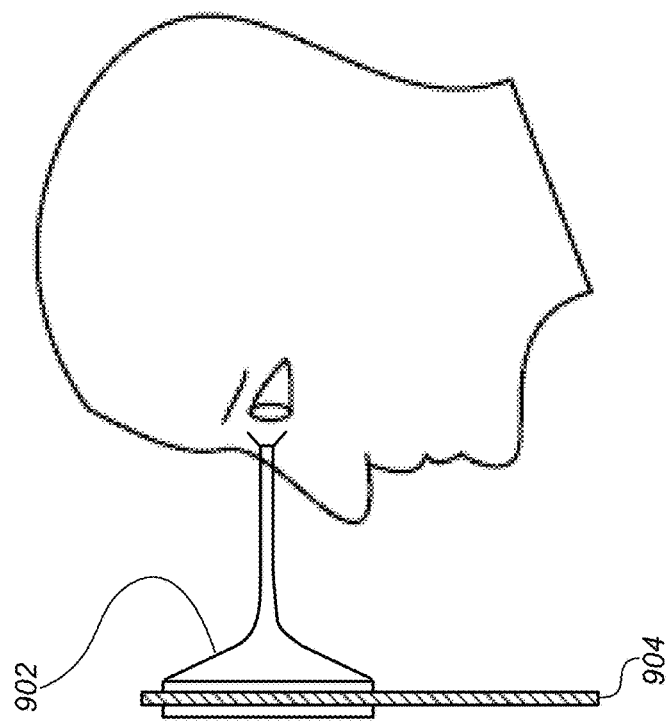
FIGS. 9A and 9B illustrate a method to perform video capture using an add-on positioning device with the PVCD according to another embodiment of the present disclosure.
Figure 9A:
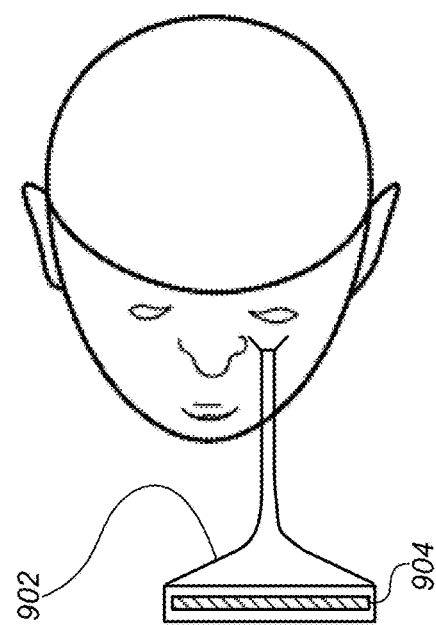

FIGS. 9A and 9B illustrate an alternative method to position the PVCD in optimal position to perform video capture using an add-on removable positioning device 902 attached to a PVCD 904. It will be appreciated that this method can be used to perform video capture using either a PVCD having rear facing camera or a front facing camera.

Figure 10:
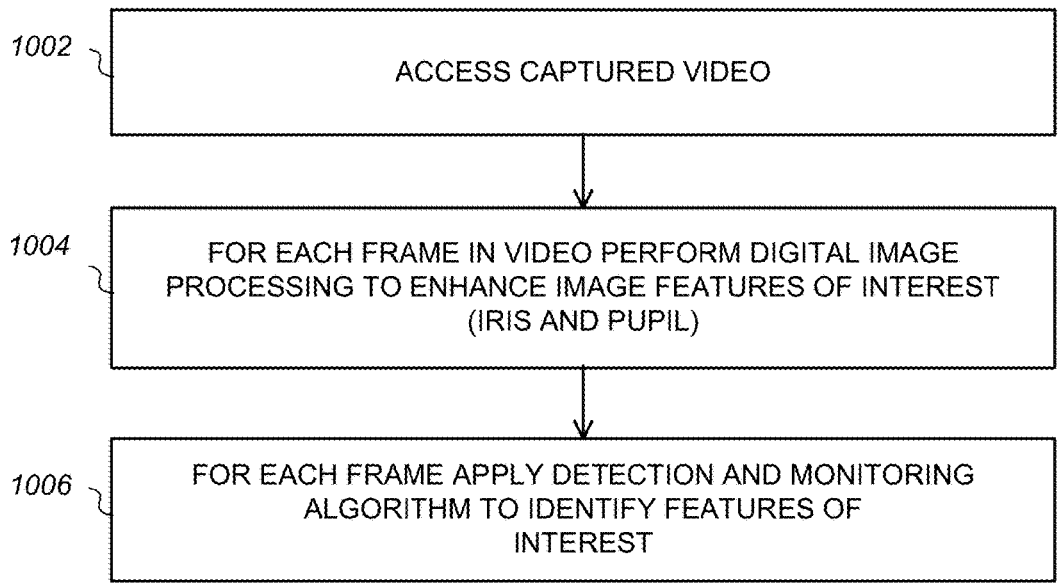
FIG. 10 is a flowchart illustrating a method to perform video processing according to an embodiment of the present disclosure.

FIG. 10 is a flowchart illustrating a method to perform video processing according to one embodiment of the present disclosure. Referring to FIG. 10, the method begins with a processor, either the local processor 208 in the PVCD or the remote processor 224, accessing captured video (1002). Typically, the captured video is stored in local memory 212; however it may alternatively be stored in remote memory 226. Next, for each frame in video digital image processing is performed using the processor to enhance image features of interest, such as the iris and pupil (1004). Finally, for each frame the processor applies a detection algorithm to identify the features of interest (1006), after which eye feature measurements are performed.

Figure 11:
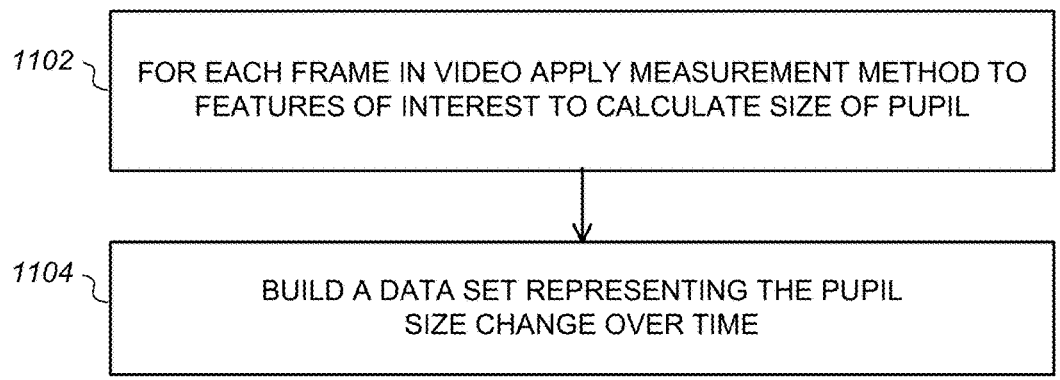
FIG. 11 is a flowchart illustrating a method to perform eye feature(s) measurements according to an embodiment of the present disclosure.

FIG. 11 is a flowchart illustrating a method to perform eye feature(s) measurements according to one embodiment of the present disclosure. Referring to FIG. 11, the method begins with the processor for each frame in the captured and processed video applying a measurement method to features of interest to calculate size of pupil for each frame (1102). Next, a data set is built representing a change in pupil size over time, such that videos captured at "n" frames per second, will provide "n" consecutive measurements representing the change in pupil size over a 1 second time period (1104).

The method consists of measuring in each frame of the captured video, both the size of the pupil and the iris and/or any other relevant image feature in the captured video that is not affected by the light stimuli, i.e., the iris. After features of interest identification, the size measurement is performed by the measurement algorithm and it may consist of counting the pixel in the image feature of interest, and/or fitting curves like circles or ellipses, or any other geometrical shape to the area and/or perimeter of the features of interest from which a size calculation is performed. After the measurements are performed a compensation algorithm will analyze the change of size of pupil and iris from frame to frame. Any change in size of iris is due to PVCD movement only, while changes in pupil size are due to both to pupil reaction to light stimuli and PVCD movements. The compensation algorithm will use the change in the size of iris to extrapolate the pupil size change due only to the light stimuli, effectively removing the effect of the PVCD movement from the pupil size measurement and provide an accurate measurement of pupil size change due to light stimuli only. The types of movements that affect the measurements are forward and backward motion, rotation around the vertical axis and tilt around the horizontal axis.

FIGS. 12A through 12D illustrate eye feature(s) measured, the effect of a light source on the eye feature(s), and methods to accurately measure change in pupil dimension in a video recording due to light stimuli while compensating measurement error due to movement of video capturing device.

Figure 12A:
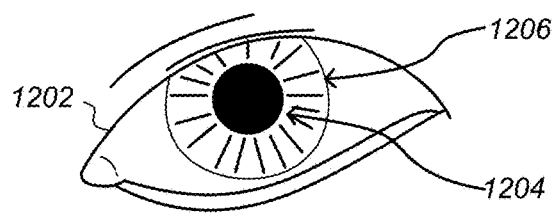
FIGS. 12A through 12D illustrate eye feature(s) measured, the effect of a light source on the eye feature(s), and the effect of PVCD movement on eye feature(s) captured according to embodiments of the present disclosure.
Figure 12B:
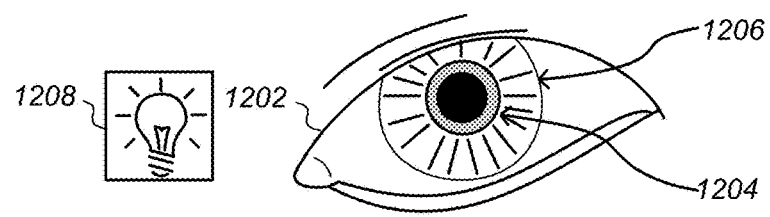

FIG. 12A shows an eye 1202 including a pupil 1204 and an iris 1206 prior to exposure to light stimuli. It is noted that the iris 1206, unlike the pupil 1204 is not affected by light. FIG. 12B shows an eye 1202 including a pupil 1204 and an iris 1206 after exposure to light stimuli from a light source 1208. It is noted that the pupil 1204 contracted.

Figure 12C:
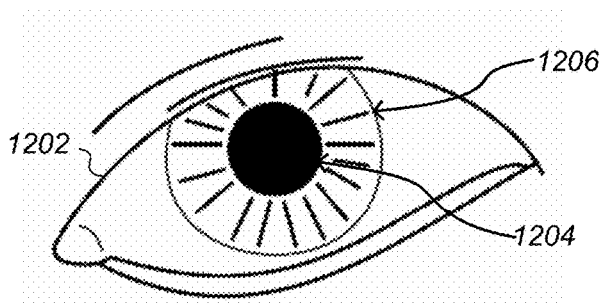
Figure 12D:
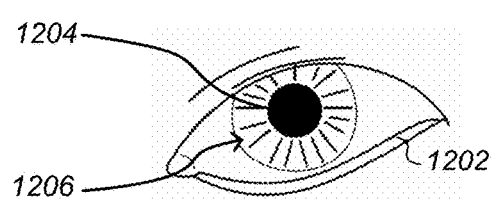

FIGS. 12C and 12D shows the effect of camera movement on pupil size and an iris 1206 in captured video frames. Referring to FIG. 12C it is noted as the camera (PVCD) moves closer to the eye both the pupil 1204 and iris 1206 get larger. FIG. 12D shows that as the camera (PVCD) moves away from the eye both the pupil 1204 and iris 1206 get smaller. Thus, in prior art approaches to measuring pupil contraction or dilation the camera was required to be fixed relative to the eye. In contrast, in the method using the system, which measures the pupil size relative to an outer edge of the iris, are therefore tolerant of movement during the predetermined time in which video is captured.

Figure 13A:
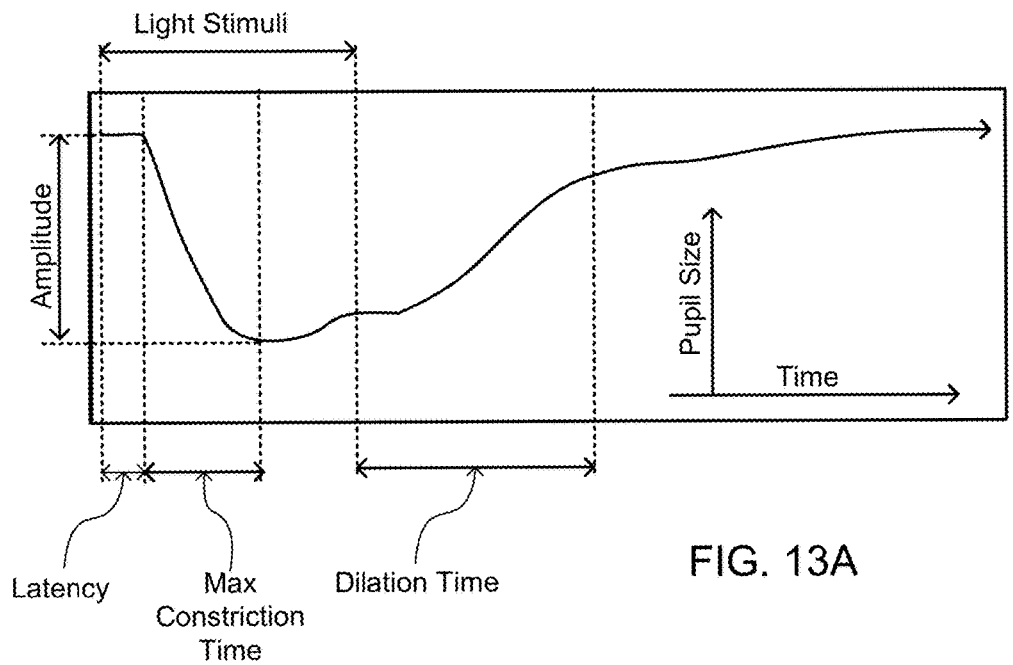
FIG. 13A is a graph of pupillary constriction measured according to embodiments of the present disclosure.
Figure 13B:
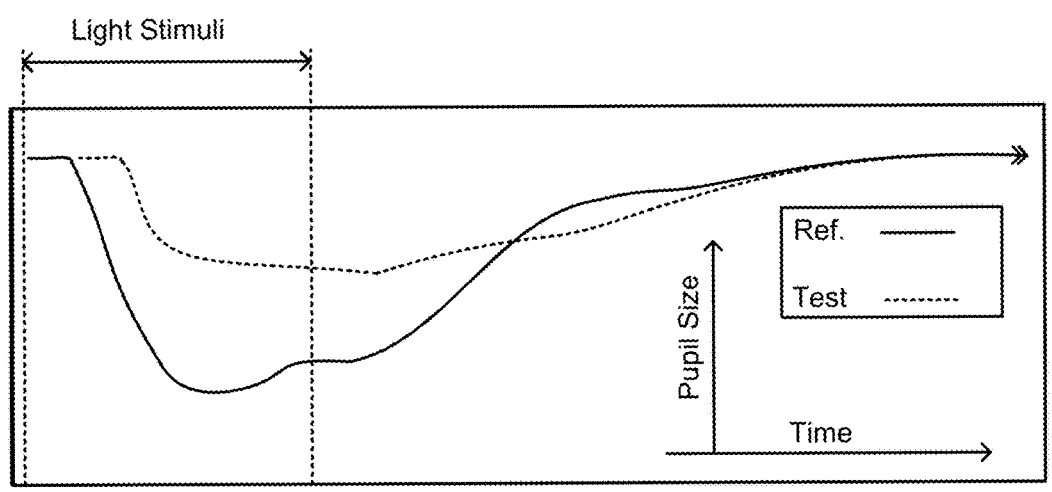
FIG. 13B is a graph of pupillary dilation following constriction measured according to embodiments of the present disclosure.

Data analysis is the process of extracting critical information from the eye features measurement process. The data analysis performed will now be described with reference to FIGS. 13A and 13B. FIG. 13A is a graph of pupillary constriction and FIG. 13B is a graph of pupillary dilation following constriction measured according to embodiments of the present disclosure.

Referring to FIG. 13A, a normal reaction to a high intensity light stimuli consist in pupillary constriction after a latency period. Referring to FIG. 13B, after constriction, pupillary re-dilation occurs and eventually the original, pre-stimulus size is reached again when the light stimuli is removed. Several parameters are calculated and stored, like amplitude, latency, max constriction time, dilation time, other parameters and variation of current test data against a Reference Data Set.

Figure 14:
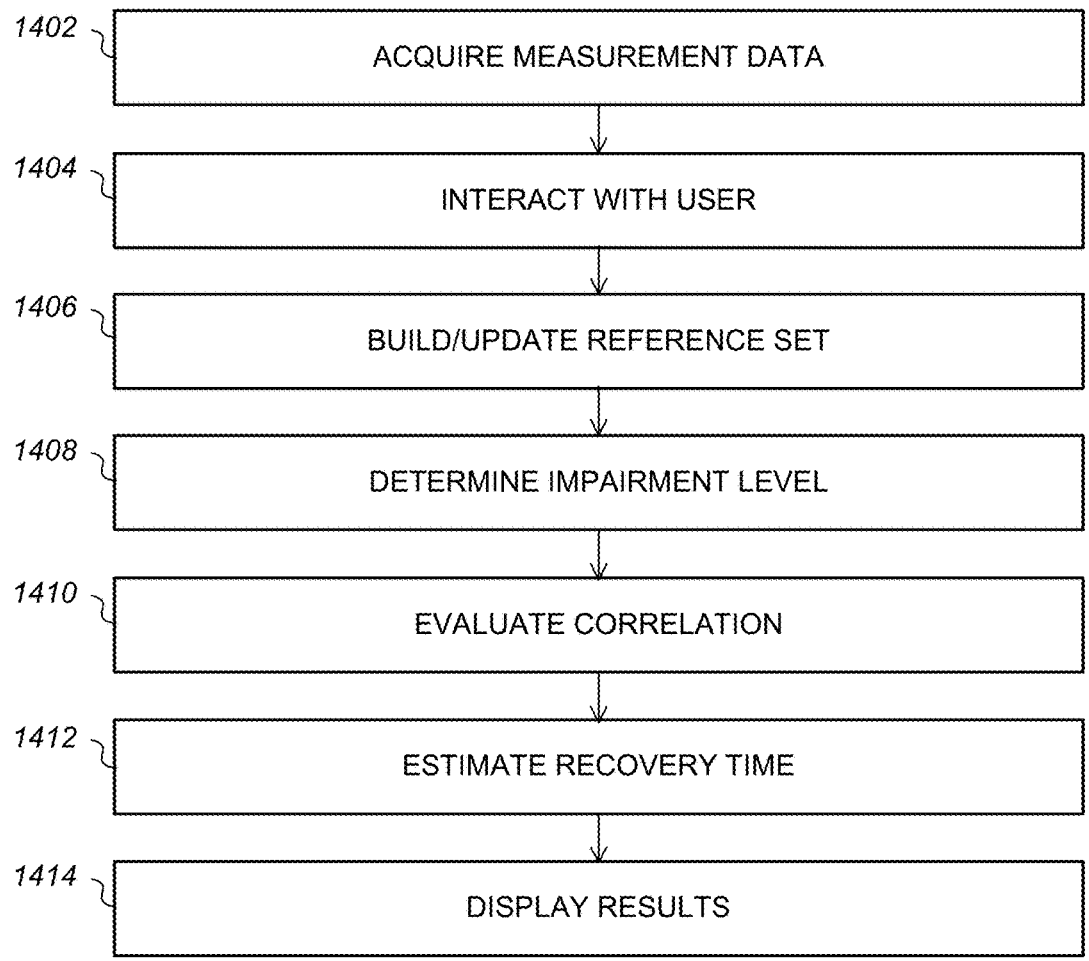
FIG. 14 is a flowchart illustrating a method to perform correlation and prediction process according to an embodiment of the present disclosure.

FIG. 14 is a flowchart illustrating a method to perform a correlation and prediction process according to one embodiment of the present disclosure. Referring to FIG. 14, the method begins with acquiring measurement data (1402). Next, the system interacts with user (1404). By interact with the user it is meant that the user interface may request additional information from the user, like activities performed before the test, if alcohol or any other substance has been consumed. This additional information is used to correlate the impairment level to other physical measurements. For example, in case of impairment due to alcohol consumption, a Blood Alcohol Concentration (BAC) value may be estimated. A reference set including reference parameters is built and/or updated (1406). Next, the level of impairment of the person undergoing test is determined by comparing calculated parameters to the reference parameters (1408), a significant variation of PLR is always an indication of some sort of impairment, subsequently with or without the additional information provided by the user, the correlation to other physical impairment alteration measures is evaluated (1410). Where the impairment is due to intoxication, a recovery time can be estimated (1412) or for some other kind of impairment a recommendation of seeking immediate medical help can be provided and/or a connection with a remote medical professional can be established to interact with the User under test via audio and/or video connection to make further analysis for diagnostic, screening and/or monitoring purposes. Finally, the results are displayed to a user (1414).

Figure 15:
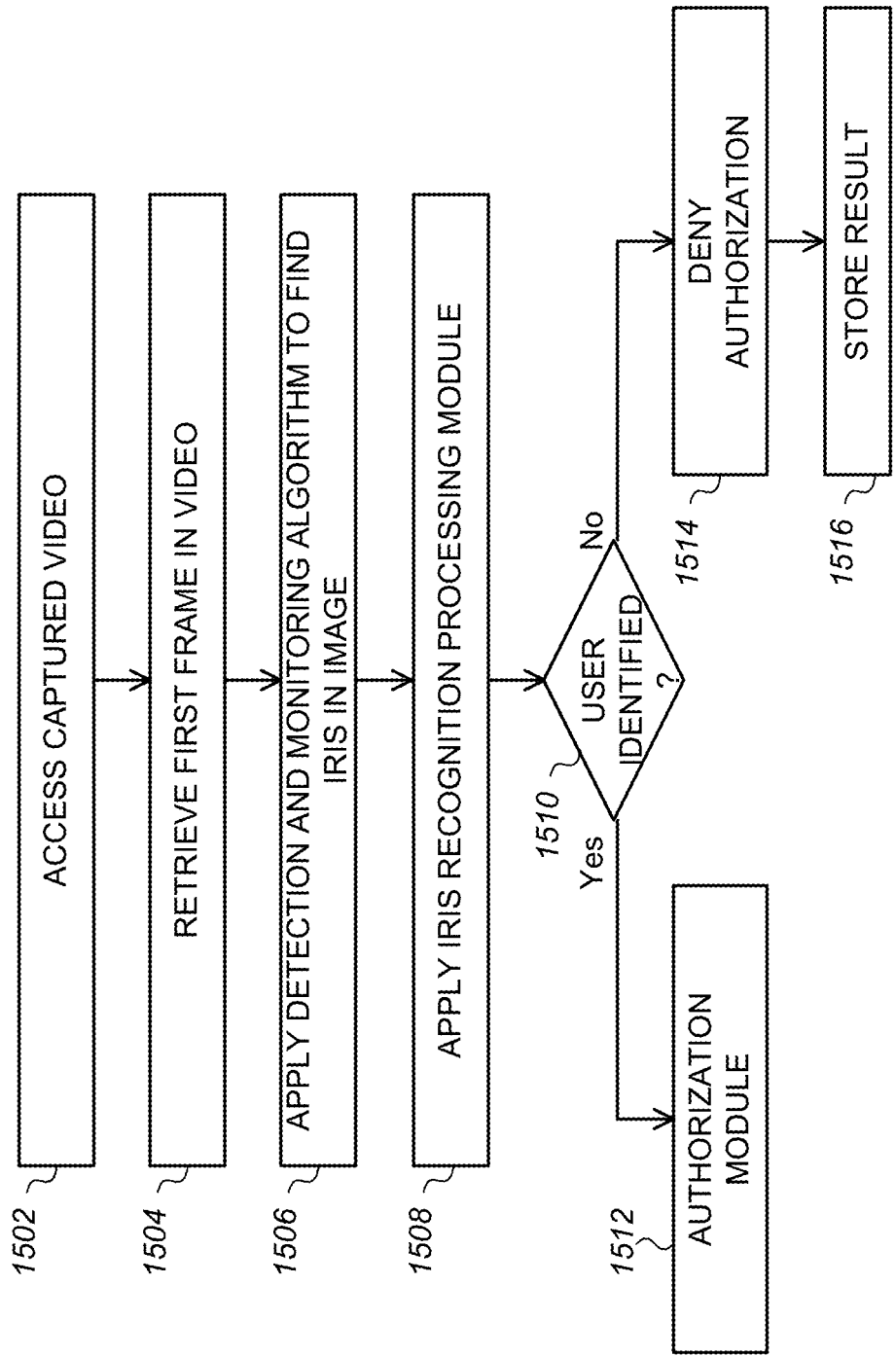
FIG. 15 is a flowchart illustrating a method to perform user identification according to an embodiment of the present disclosure.

FIGS. 15 and 16 illustrate an alternative method further including software modules to perform user identification and authorization using captured image or video from the PVCD. In particular, FIG. 15 is a flowchart illustrating a method to perform user identification through iris recognition according to an embodiment of the present disclosure. FIG. 16 is a flowchart illustrating a method to perform user authorization according to an embodiment of the present disclosure. It will be understood that the user identification or iris recognition software or module, and the authorization software or module can be either in the local memory 212 or the remote memory 226 shown in FIG. 2.

Referring to FIG. 15, the process begins with user identification through iris recognition with access the captured video (1502) and retrieving the first frame in that video (1504). Next, the detection algorithm is applied to find an iris in the image of the first frame (1506). An iris recognition processing software or module is then used to compare the iris in the image of one or several frames, to a stored image of the user. Once the user has been identified, i.e., the iris in the image of the captured frames matches a stored image of the user (1510), the method proceeds to the authorization software or module (1512) to begin testing. If the iris in the image of the first frame does not match the stored image of the user, authorization is denied (1514), and the result, the failed authorization attempt is stored (1516).

Referring to FIG. 16, once the user has been positively identified (1602), the eye feature measurement is performed (1604) and an impairment level determined (1606). The eye feature measurement and determination of impairment level can be accomplished using the methods, processes and algorithms described above with reference to FIGS. 1, 4 and 14. Once the user identity has been confirmed, i.e., the iris in the video matches a stored image of the user (1608), the method proceeds to the release authorization (1610) and the results of the eye feature measurement and determination of impairment level are stored (1612). If the user identity has been confirmed, i.e., the iris in the video does not match the stored image of the user, authorization is denied (1614), and the result, the failed authorization attempt.

Optionally, where the PVCD is a network enabled device, such as a smartphone, the method can further include providing contact information or even automatically connect to network enabled transportation, emergency services, and/or to or a trusted personal contact previously given by the person undergoing test to render assistance, and/or to connect with a remote medical professional that will interact with the User under test via audio and/or video connection to make further analysis for diagnostic, screening, authorization and/or monitoring purposes.

Optionally where the invention may be used in safety sensitive environments, where for safety and liability reasons, an employee starting a working shift is required to self-test and submit the result to an employer to receive authorization to work.

Figure 17A:
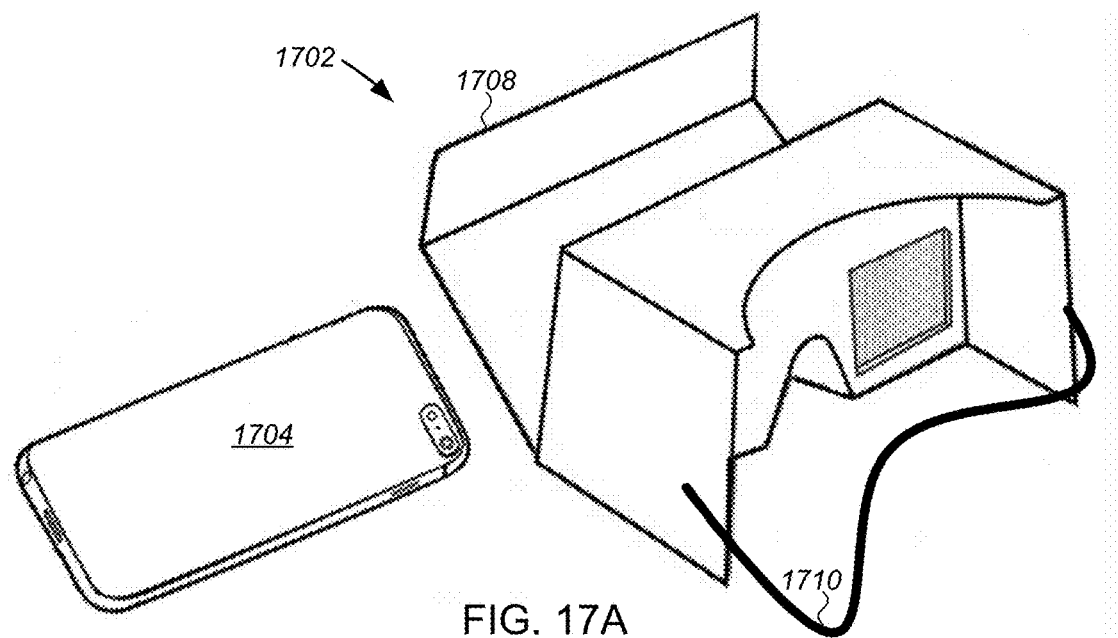
FIGS. 17A and 17B illustrate use of an add-on enclosure with the PVCD to position and control light conditions for video capture according to another embodiment of the present disclosure.
Figure 17B:
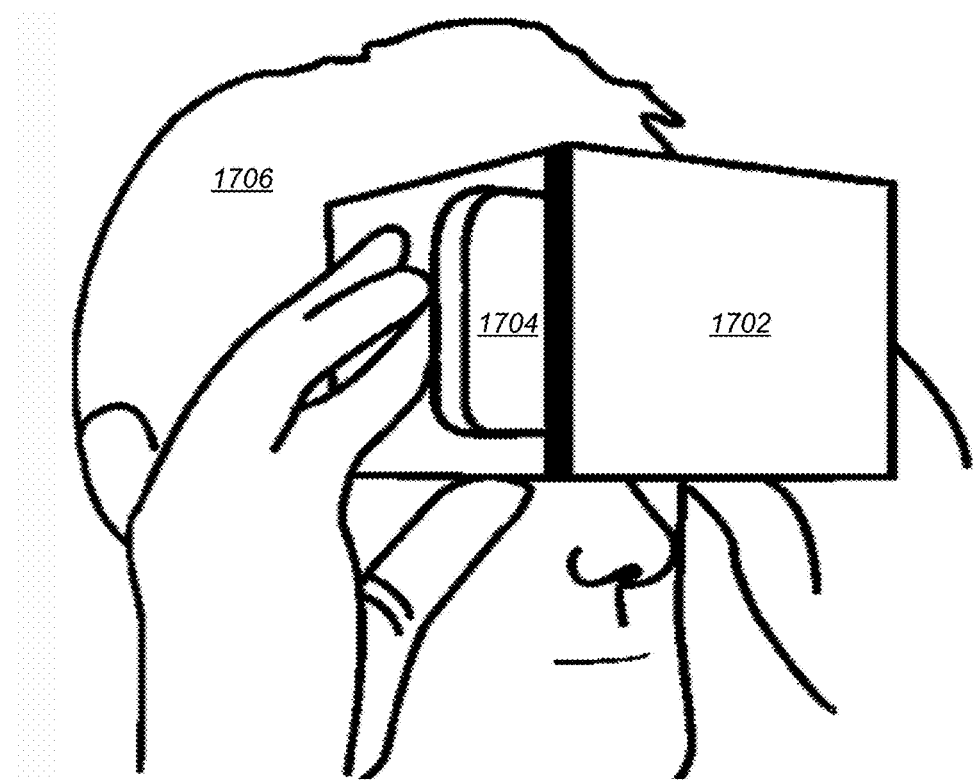

FIGS. 17A and 17B illustrate use of an alternative add-on positioning device or enclosure 1702 removably attached to a PVCD 1704 to position the PVCD in optimal position and control light conditions for video capture. Although shown and described with reference to a PVCD having a rear facing camera, it will be appreciated that this method can be performed using either a PVCD having rear facing camera or a front facing camera. In the embodiment shown, the enclosure 1702 is adapted to cover or enclose both eyes and at least a portion of a face of the user 1706 when held to position PVCD 1704 in optimal position. By optimal position it is meant the enclosure positions a camera of the PVCD 1704 in optimal vertical and horizontal position, and at an optimal distance for video capture. The optimal distance for video capture is the minimum focal distance supported by the PVCD camera. The enclosure 1702 is opaque to control light conditions by substantially excluding ambient light, thereby providing complete or near darkness for the eyes. Generally, the enclosure 1702 is made of a thin, stiff plastic or cardboard, and includes a hinged portion 1708, as shown in FIG. 17A, or a slot into which the PVCD 1704 inserted or held. Preferably, the enclosure 1702 is sized to accommodate PVCDs, such smartphone, of different sizes. More preferably, the enclosure 1702 is collapsible to allow the enclosure to be stored or carried in a substantially flat package or format. Optionally, the enclosure 1702 may further include a headband or strap 1710 by means of which the enclosure can be affixed to cover the eyes and at least a portion of the face of the user 1706.

Figure 18A:
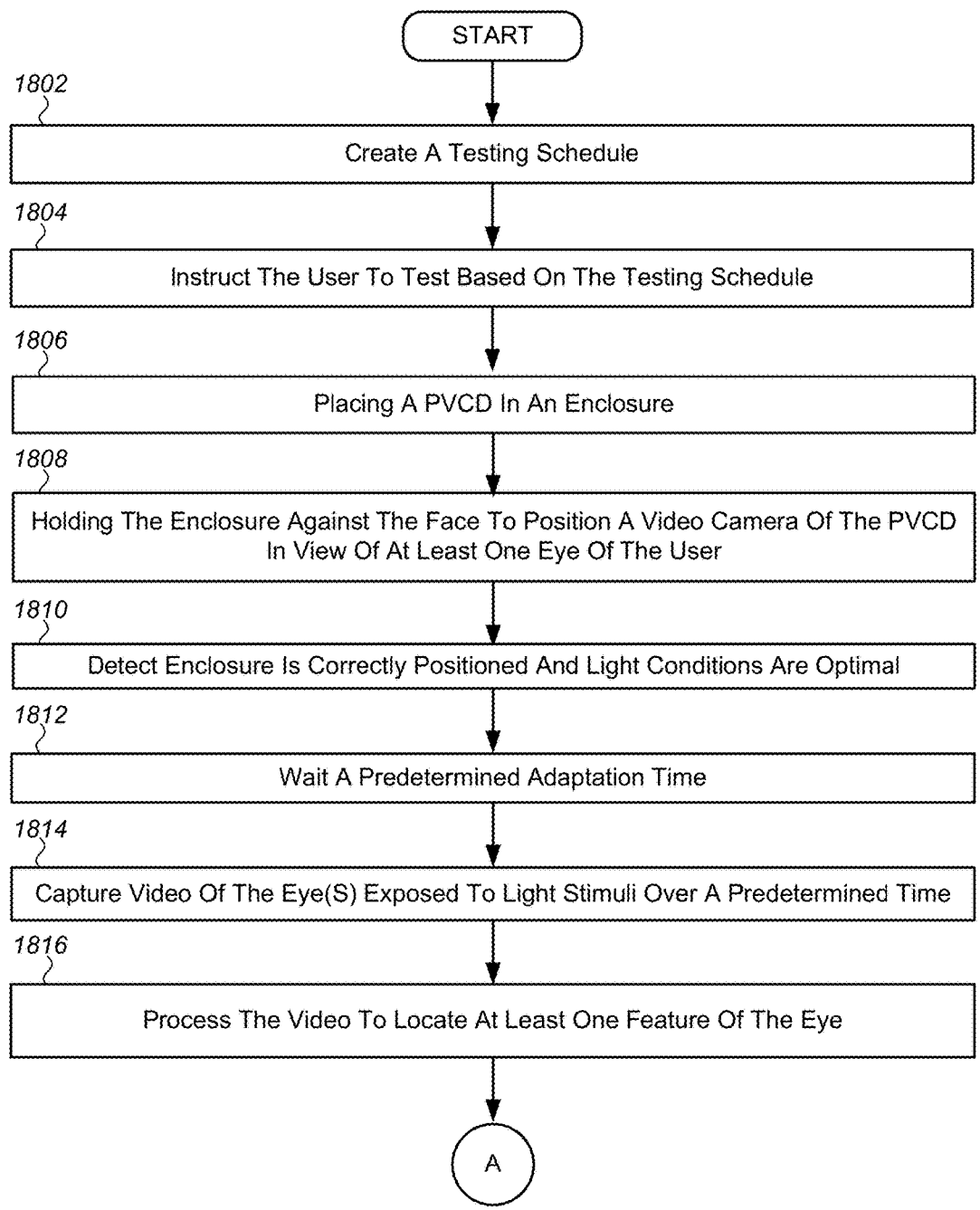
FIGS. 18A and 18B is a flowchart illustrating a method to perform impairment test using the enclosure of FIGS. 17A and 17B according to an embodiment of the present disclosure.
Figure 18B:
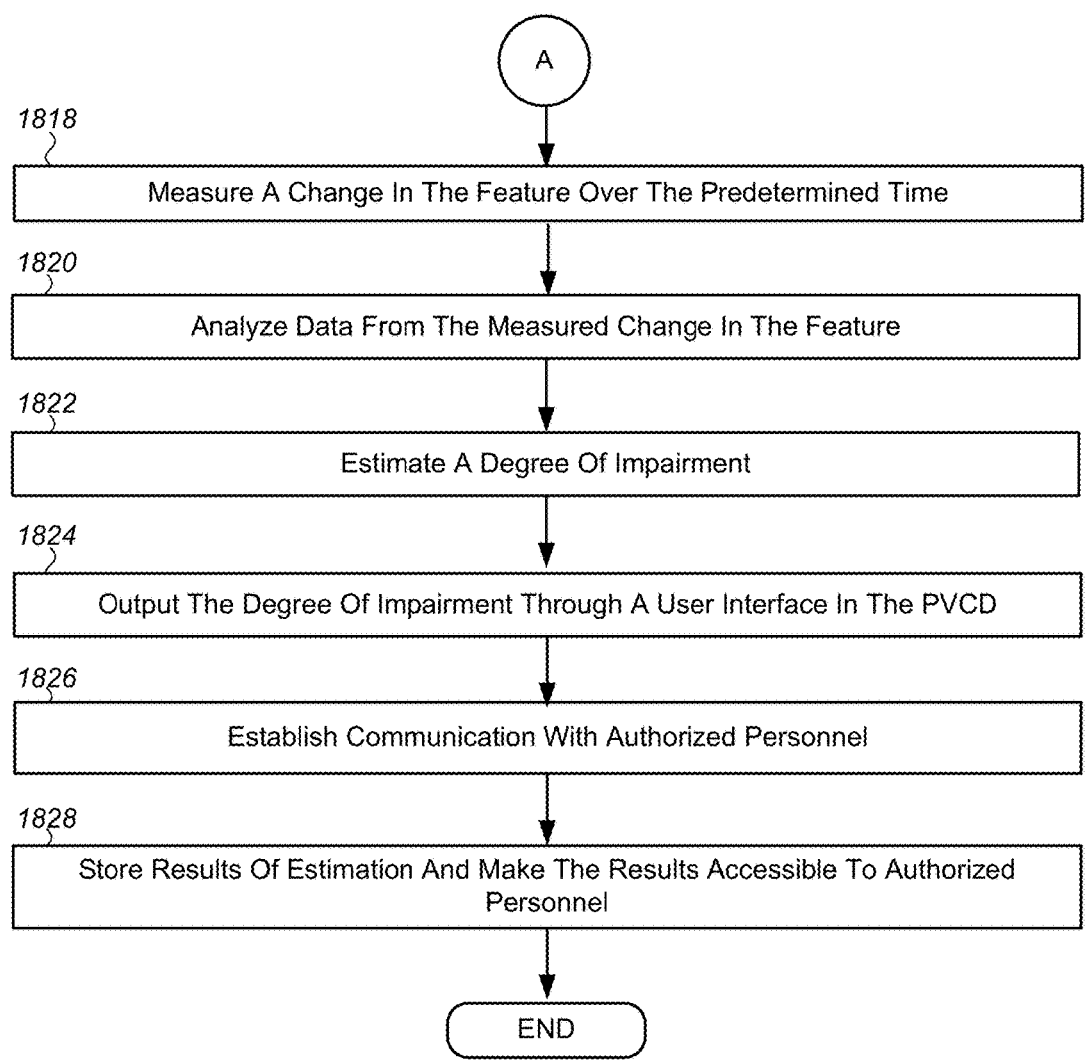

The enclosure 1702 can be configured to position the PVCD 1704 for either single eye video capture or simultaneous video capture of both eyes, depending on the placement of the PVCD within the enclosure relative to a location of the camera in the PVCD. For example, where the PVCD 1704 is a smartphone 300 such as shown in FIG. 3A, having a rear-facing video camera 302 and light source 304 near a top edge of the front face, the enclosure 1702 is adapted or configured as shown in FIG. 17A to hold the smartphone so that the camera location is nearer to the center of the enclosure to facilitate simultaneous video capture of both eyes and a majority of the portion of the face covered by the enclosure. However, it will be understood that depending on the distance at which the PVCD 1704 is held away from the eyes and face of the user by the enclosure 1702, and a viewing angle of the camera, the PVCD/smartphone does not need to be held or positioned by the enclosure so that the camera is exactly at the center of the enclosure. Indeed, it is possible that for single eye measurement the PVCD/smartphone is held so that the camera is positioned in front of the eye under test FIGS. 18A and 18B is a flowchart illustrating a method to perform a PLR alteration test using the enclosure of FIGS. 17A and 17B according to an embodiment of the present disclosure. Although not shown in these figures, it will be understood that as described above with reference to FIG. 1 the method can, and generally does, include an initial step of receiving from the user data on the person undergoing the impairment test. User data can include a name of the person undergoing the impairment test, contact information, age, gender, height, weight, body mass, ethnicity, and other information required for the correlation and prediction step.

Referring to FIG. 18A, the method begins with the optional steps of creating a testing schedule (1802), and instructing a user to test for PLR alteration based on the testing schedule (1804). The testing schedule can be created by the user, or by an authorized person, such as an employer, family member, medical professional or officer of a court or law. The testing schedule can be randomized, scheduling tests at any time of a day, week or month with any interval of time passing between sequential tests. Alternatively, the test schedule can be regular, scheduling tests at a fixed time of day, week or month. For example, an employer may schedule a PLR alteration test with the purpose of detect on-the-job impairment to be performed at or prior to the beginning of a work shift or work week. Alternatively, a medical professional may schedule a PLR alteration test for a patient at regular times over a period of time to monitor the progression of a neurological disorder. Where the PVCD 1704 includes text, audio and/or video communication capability, and the step of instructing the user to test for impairment based on the testing schedule may be performed using a notification or reminder sent through the PVCD. Generally, the instruction to the user includes a predetermined time frame or interval, set for example by a party creating the testing schedule, in which the testing must begin and/or be completed.

Next, the PVCD 1704 is placed or positioned in an enclosure 1702 (1806). As described above with reference to FIGS. 17A and 17B, the enclosure 1702 is adapted to position a video camera of the PVCD 1704 in optimal position when held against a face of the user 1706. Additionally, the enclosure 1702 can be nearly opaque or opaque to control light conditions during testing by substantially excluding ambient light, thereby providing complete or near complete darkness for the eyes.

The user then holds or affixes the enclosure against their face to cover or encloses at least one eye and a portion of the face (1808). The enclosure 1702 may be affixed by a strap 1710 as described above with reference to FIG. 17A. The enclosure 1702 is adapted or configured so that when held against the face a video camera of the PVCD 1704 is positioned to have a view of at least one eye of the user 1706, and to shade the eye from ambient light. More preferably, as described above, the enclosure 1702 is adapted to position the video camera of the PVCD 1704 to have a view of one or both eyes and at least a portion of the user's 1706 face.

Next, the correct positioning of the enclosure 1702 on the face of the user 1706 and optimal light conditions are detected (1810). This detection can be accomplished, for example, using the video camera of the PVCD 1704 to detect at least one eye is in view, and/or the camera or another light sensor to detect that no significant ambient light is leaking into the enclosure 1702.

After waiting or performing a countdown for a predetermined adaptation time (1812), the eye or eyes are exposed to light stimuli over another predetermined time using the PVCD and video or multiple images of the eye(s) captured exposed to light stimuli over a predetermined time using the video camera of the PVCD 1704 (1814). The adaptation time allows the eyes to adapt to new light conditions created by the enclosure 1702. Alternatively, the predetermined adaptation time can be variable based on a measurement or estimate of ambient light conditions outside the enclosure 1702 using sensors or a camera of the PVCD 1704 either not enclosed by the enclosure, for example an exposed rear facing camera of the PVCD held in the enclosure in a front facing orientation, or made by sensors or a camera of the PVCD prior to inserting the PVCD in the enclosure or holding or affixing the enclosure against the face of the user 1706. The steps of exposing the eyes to light stimuli and video capture over the predetermined time using the PVCD 1704 are generally the same as those described above with reference to FIGS. 1 and 4.

The captured video is then processed to locate at least one feature of at least one of the eyes (1816). As described above with reference to FIGS. 1 and 10, the features of the eye located can include a pupil, an iris and/or a border between the pupil and the iris or any other discernible feature. Optionally or preferably, the video capture (step 1814) and processing of the captured video (step 1816) can include simultaneously capturing video of both eyes, and processing the video to locate at least one feature of each of the eyes. It will be understood that this embodiment enables two dual, simultaneous testing for PLR alteration, thereby improving accuracy of the test results. Additionally, this embodiment enables a comparison to be made between the PLR of each eye, either as a further indication of impairment.

Optionally, the method can further include a step (not shown in the flowchart of FIGS. 18A and 18B) of authenticating or identifying the user 1706 based on features captured in video and the method described above with reference to FIG. 15. It will be understood that an embodiment of the method using this step would be particularly desirable where the testing for impairment is being done at the request of someone other than the user 1706.

Referring to FIG. 18B, changes in the located feature(s) of one or both eyes in response to the light stimuli over the predetermined time is measured (1818). Generally, this step can be accomplished as described above with reference to FIGS. 1 and 11-13B. Data extracted from the measured change in the feature is then analyzed (1820). The data analysis can include calculating a number of parameters from the extracted data. Next, the calculated parameters are correlated with predetermined reference parameters in a data-store and an estimate of a degree of impairment made based on the results of the correlation (1822). Finally, the resultant probability and degree of impairment of the person, is output through a user interface in the PVCD 1704, such as a display and/or auditory interface to the user 1706 (1824). It is noted that user may be the person undergoing the impairment test or another individual.

Optionally, as shown in FIG. 18B, where the PVCD 1704 includes text, audio and/or video communication capability the method may further include the additional steps of establishing communication with authorized legal, medical or support personnel for further analysis of the estimated degree of impairment, for diagnostic, screening, authorization or monitoring purposes (1826), and/or where the PVCD includes memory storing results of the estimated degree of impairment locally, and making the results remotely accessible to authorized personnel over a cellular or computer network (1828).

Figure 19:
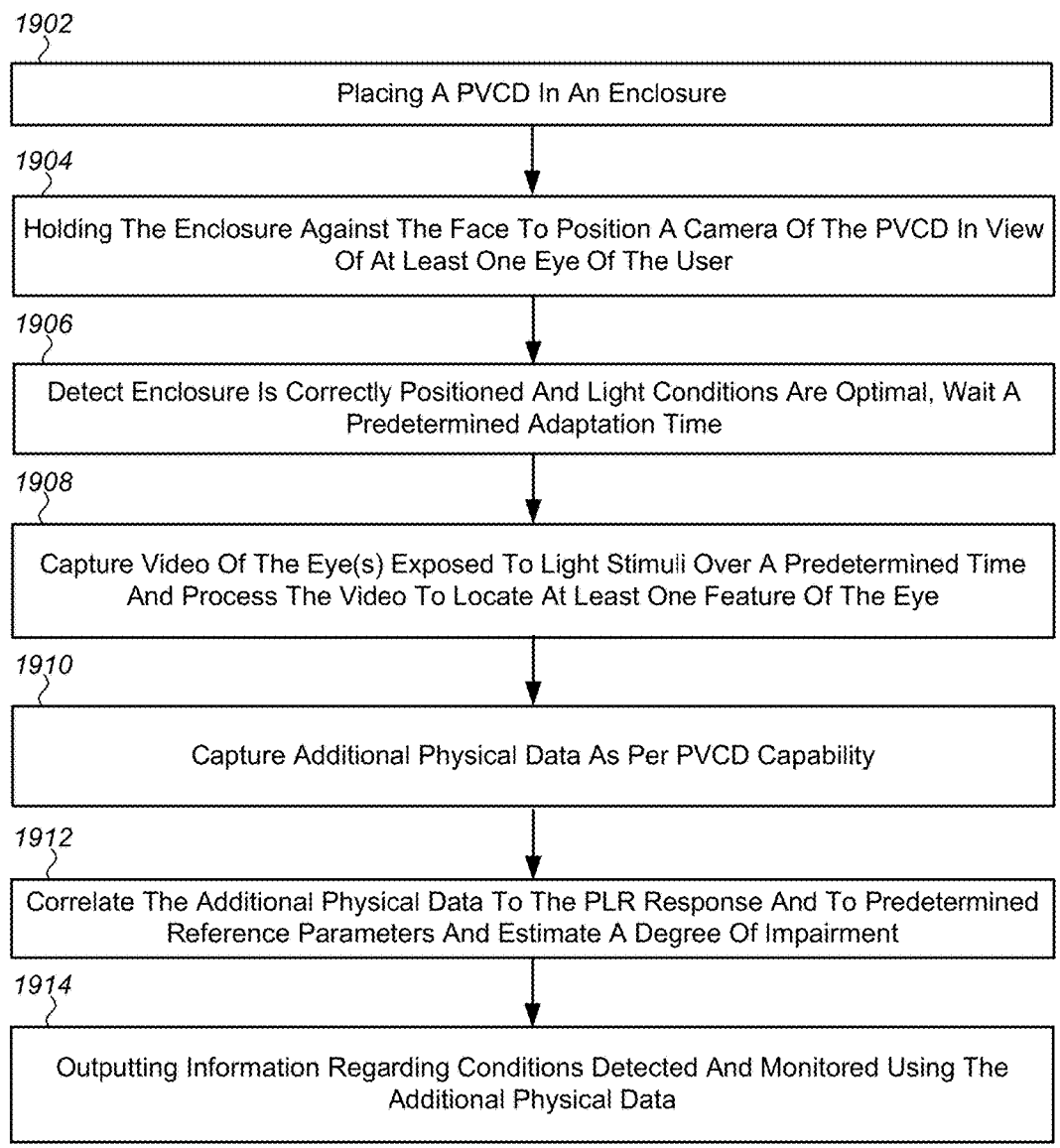
FIG. 19 is a flowchart illustrating a method to collect additional physical data on a condition of a user according to an embodiment of the present disclosure.

In yet another embodiment, the test for impairment may further include steps to collect additional physical data of the user to be combined with the estimated degree of impairment for further diagnostic or monitoring purposes. The PVCD can include additional sensors, such as an accelerometer, and software to collect additional physical data with or without additional attachments. For example, the PVCD can be paired with a separate wearable device, such as a fitness tracker or watch, capable of measuring one or more of a hand tremor, pulse rate, oxygenation level, and irregular heartbeat. An embodiment of a method including these steps will now be described with reference to the flowchart of FIG. 19. Referring to FIG. 19, the method can begin with placing or positioning the PVCD 1704 in an enclosure 1702 (1902); holding or affixing the enclosure to cover or enclose at least a portion of the face, such that the video camera of the PVCD is in view of at least one eye of the user (1904); detecting that enclosure is correctly positioned on the face and light conditions are optimal, and waiting or performing a countdown for a predetermined adaptation time (1906); exposing the covered portion of the user's face to light stimuli, capturing video or multiple images of the face and eye over a predetermined time and processing the video to locate at least one feature of the eye using the PVCD 1704 (1908); capture additional physical data per PVCD capability (1910); correlate the additional physical data to the PLR response and to predetermined reference parameters and estimate a degree of impairment (1912); and output information regarding conditions detected and monitored using the additional physical data (1914). Generally, these steps can be accomplished similar to steps described above with reference to FIGS. 18A and 18B.

The additional physical data captured by the PVCD 1704 (step 1910) can include data collected using photoplethysmography (PPG). By PPG it is meant an optical technique that can be used to detect changes in blood volume and/or light absorption in the dermis and subcutaneous tissue of skin of, for example in the face or a finger. It is often used to non-invasively to detect and make measurements of a heartbeat. It is also possible to detect and measure an oxygen concentration in the blood by detecting changes in light absorption. Thus, the additional physical data collected using the PVCD 1704 and PPG can include a blood oxygenation level, a pulse rate and an irregular heartbeat, such as that caused by arterial fibrillation (AF).

Where the PVCD 1704 includes an accelerometer, the additional physical data can include data on hand tremor, and the method can begin with collecting data on hand tremor by having the user 1706 attempt to hold the PVCD using a single hand in fixed or stable position for a predetermined period of time. For example, the user 1706 may be instructed to hold the PVCD 1704 in front of their body for a period of several seconds. It will be understood that this step can be performed prior to or after affixing the PVCD 1704 in the enclosure 1702, and either before or after performing other steps of the impairment test.

Optionally or additionally, information regarding conditions detected and monitored using the additional physical data can be shared with authorized personnel using communication established through the PVCD 1704, and/or stored locally in a memory of the PVCD, which can then be accessed remotely by authorized personnel over a cellular or computer network.

Thus, embodiments of to a system and method for testing for PLR alteration due to the influence of alcohol, drugs, an injury, fatigue and or neurological disorder have been described. Although the present disclosure has been described with reference to specific exemplary embodiments, it will be evident that various modifications and changes may be made to these embodiments without departing from the broader spirit and scope of the disclosure. Accordingly, the specification and drawings are to be regarded in an illustrative rather than a restrictive sense.

The Abstract of the Disclosure is provided to comply with 37 C.F.R. § 1.72(b), requiring an abstract that will allow the reader to quickly ascertain the nature of one or more embodiments of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Reference in the description to one embodiment or an embodiment means that a particular feature, structure, or characteristic described in connection with the embodiment is included in at least one embodiment of the circuit or method. The appearances of the phrase one embodiment in various places in the specification do not necessarily all refer to the same embodiment.

What is claimed is:

1. A method of testing a user for impairment comprising:
   placing a portable video capture device (PVCD) in an opaque enclosure;
   positioning the opaque enclosure over at least one eye of the user to shade the eye from ambient light;
   capturing multiple images of the eye exposed to light stimuli over a predetermined time using a camera of the PVCD;
   processing the multiple images to locate at least one feature of the eye;
   measuring a change in the feature over the predetermined time in response to the light stimuli; and
   analyzing data from the measured change in the feature, wherein analyzing data includes extracting data from the measured change in the feature, calculating a number of parameters from the extracted data, correlating the calculated parameters against predetermined reference parameters and estimating a degree of impairment for diagnostic, screening, authorization or monitoring purposes.

2. The method of claim 1, wherein the PVCD automatically detects that the enclosure containing the PVCD is positioned enclosure over the eye of the user by detecting near darkness within the enclosure and initiates a countdown for a predetermined period of time to ensure the eye has adapted to light conditions created by the enclosure before capturing multiple images of the eye exposed to light stimuli.

3. The method of claim 2, wherein the PVCD automatically detects when the enclosure is no longer correctly positioned enclosure over the eye of the user by detecting light above a predetermined threshold in the enclosure, and stops the countdown.

4. The method of claim 1, further comprising collecting additional physical data of the user to be combined with the estimated degree of impairment for diagnostic or monitoring purposes.

5. The method of claim 4, wherein the PVCD includes an accelerometer, and wherein the additional physical data includes data on hand tremor measured while the user is holding the PVCD.

6. The method of claim 4, wherein the PVCD is capable of measuring pulse rate, oxygenation level or an irregular heartbeat, and wherein the additional physical data includes a pulse rate, a blood oxygenation level or an irregular heartbeat detected using the PVCD.

7. The method of claim 4, wherein the PVCD is paired with a separate wearable device capable of measuring one or more of a hand tremor, pulse rate, oxygenation level, and irregular heartbeat.

8. The method of claim 4, wherein any additional physical data is analyzed, wherein analyzing said additional physical data include correlating the additional physical data to the measured change in the feature of the eye, and correlating the additional physical data to predetermined additional reference parameters to estimate a degree of impairment.

9. The method of claim 1, wherein the PVCD includes text, audio or video communication capability, and wherein the method further comprises establishing communication with authorized medical, legal or support personnel for further analysis of the estimated degree of impairment, diagnostic or monitoring purposes.

10. The method of claim 1, wherein the PVCD includes memory to store locally results of the estimated degree of impairment, and wherein the method further comprises making the results remotely accessible authorized medical, legal or support personnel over a cellular or computer network.

11. The method of claim 1, wherein the PVCD includes text, audio or video communication capability, and wherein the method further comprises initial steps of:
creating a regular or randomized testing schedule; and
using the PVCD instructing the user to test for impairment based on the testing schedule.

12. A system comprising:
a portable video capture device (PVCD) including a user interface, a video capture device, a light source, and a local processor;
an opaque enclosure to position the PVCD over both eyes and at least a portion of a face of a user; and
a software program and executed by the local processor, the software program including:
a video capture software to capture video of an eye exposed to light stimuli from the light source over a predetermined time using the video capture device of the PVCD;
local correlation and prediction software to: locate a feature of the eye; measure a change in the feature over the predetermined time in response to a light stimuli from the light source; extract data from the measured change in the feature; calculate a number of parameters from the extracted data; correlate the calculated parameters with predetermined reference parameters and predict a degree of impairment based on results of the correlation; and
a user interface software to output a probability and degree of impairment to the user.

13. The system of claim 12, wherein the software program further comprises computer program code to collect additional physical data on the user using the PVCD or a paired wearable device.

14. The system of claim 13, wherein the additional physical data includes a pulse rate, a blood oxygenation level, an irregular heartbeat or a hand tremor.

15. The system of claim 13, wherein the software program further comprises computer program code to analyzing data from the measured changes in light from the light source reflected from the portion of the face to collect additional physical data on the user using photoplethysmography (PPG).

16. The system of claim 15, wherein the additional physical data includes a pulse rate, a blood oxygenation level, an irregular heartbeat or a hand tremor.

17. The system of claim 13, wherein the PVCD includes text, audio or video communication capability, and wherein the software program further comprises computer program code to establish communication with authorized medical, legal or support personnel for further analysis of the estimated degree of impairment, and diagnostic or monitoring purposes of the additional physical data.

18. A method comprising:
placing a portable video capture device (PVCD) in an opaque enclosure;
positioning the opaque enclosure over eyes and at least a portion of a face of a user;
capturing video of the eyes and the portion of the face exposed to light stimuli from the PVCD over a predetermined time using a video camera of the PVCD;
processing the video and measuring changes in at least one feature of at least one eye, and in light reflected from the portion of the face;
analyzing data from the measured changes in at least one feature of at least one eye to estimate a degree of impairment based on a pupillary light reflex (PLR); and
analyzing data from the measured changes in light reflected from the portion of the face to collect additional physical data on a condition of the user using photoplethysmography (PPG);
outputting to the user through a user interface in the PVCD the estimated degree of impairment and the additional physical data.

19. The method of claim 18, wherein the additional physical data includes a pulse rate, a blood oxygenation level or an irregular heartbeat detected using the PVCD and PPG.

20. The method of claim 19, wherein the PVCD includes text, audio or video communication capability, and wherein the method further comprises establishing communication with authorized medical, legal or support personnel for further analysis of the estimated degree of impairment, and diagnostic or monitoring purposes of the additional physical data.

* * * * *